US009869669B2

United States Patent
Han et al.

(10) Patent No.: US 9,869,669 B2
(45) Date of Patent: Jan. 16, 2018

(54) BIOMARKER SENSING BASED ON NANOFLUIDIC AMPLIFICATION AND RESONANT OPTICAL DETECTION

(71) Applicant: STC.UNM, Albuquerque, NM (US)

(72) Inventors: Sang M. Han, Albuquerque, NM (US);
Cornelius F. Ivory, Pullman, WA (US);
Mani Hossein-Zadeh, Albuquerque, NM (US)

(73) Assignees: STC.UNM, Albuquerque, NM (US);
WASHINGTON STATE UNIVERSITY, Pullman, WA (US)

(*) Notice: Subject to any disclaimer, the term of this patent is extended or adjusted under 35 U.S.C. 154(b) by 632 days.

(21) Appl. No.: 14/380,350

(22) PCT Filed: Mar. 15, 2013

(86) PCT No.: PCT/US2013/032519
§ 371 (c)(1),
(2) Date: Aug. 21, 2014

(87) PCT Pub. No.: WO2013/169393
PCT Pub. Date: Nov. 14, 2013

(65) Prior Publication Data
US 2015/0024507 A1    Jan. 22, 2015

Related U.S. Application Data

(60) Provisional application No. 61/643,828, filed on May 7, 2012.

(51) Int. Cl.
*B01L 3/00* (2006.01)
*G01N 21/75* (2006.01)
(Continued)

(52) U.S. Cl.
CPC ........ *G01N 33/5302* (2013.01); *G01N 21/75* (2013.01); *G01N 21/7746* (2013.01);
(Continued)

(58) Field of Classification Search
CPC .. B01L 3/502753; B01L 3/5027; B01L 3/502; B01L 3/50; G01N 33/5302;
(Continued)

(56) References Cited

U.S. PATENT DOCUMENTS 7,796,262 B1    9/2010  Wang et al.
8,105,471 B1 *  1/2012  Han ................. G01N 27/44752
                                                  204/451

(Continued)

FOREIGN PATENT DOCUMENTS

WO    2008-043040    4/2008

OTHER PUBLICATIONS

International Search Report dated Jul. 9, 2013 from International Application No. PCT/US2013/032519, pp. 1-11.
(Continued)

*Primary Examiner* — Christine T Mui
(74) *Attorney, Agent, or Firm* — MH2 TECHNOLOGY LAW GROUP, LLP

(57) ABSTRACT

Provided is a sensor platform that includes a substrate, a plurality of nanochannels disposed on the substrate, and a plurality of electrodes, a waveguide disposed on the substrate and an analysis chamber and a reference chamber disposed on the substrate. Each electrode extends substantially across a width of the plurality of nanochannels. At least one analysis optical resonator is disposed in the analysis chamber and is optically coupled to at least a portion of the waveguide. The at least one analysis optical resonator is in fluid communication with at least one of the plurality of nanochannels. At least one reference optical resonator is
(Continued)

disposed in the reference chamber and is optically coupled to at least a portion of the waveguide. The at least one reference optical resonator is in fluid communication with at least one other of the plurality of nanochannels.

13 Claims, 14 Drawing Sheets

(51) Int. Cl.
*G01N 33/53* (2006.01)
*G01N 21/77* (2006.01)
*G01N 33/543* (2006.01)

(52) U.S. Cl.
CPC ... *G01N 33/5438* (2013.01); *G01N 33/54373* (2013.01); *B01L 3/502753* (2013.01); *G01N 2021/755* (2013.01)

(58) Field of Classification Search
CPC ........ G01N 33/53; G01N 33/50; G01N 33/48; G01N 21/75; G01N 2021/755

USPC ............. 422/68, 68.1, 50, 502; 436/149
See application file for complete search history.

(56) References Cited

U.S. PATENT DOCUMENTS

| | | | |
|---|---|---|---|
| 2005/0013529 A1* | 1/2005 | Chiu | G02B 6/29341 385/15 |
| 2006/0170931 A1 | 8/2006 | Guo et al. | |
| 2010/0015741 A1* | 1/2010 | Krug | G02B 6/12007 438/31 |

OTHER PUBLICATIONS

Erickon et al. Nanobiosensors: optofluidic, electrical and mechanical approaches to biomolecular detection at the nanoscale. Microfluid Nanofluid, 2008, vol. 4, No. 1-2, pp. 33-52.

Mandal et al. Nanoscale optofluidic sensor arrays for dengue virus detection. Proceedings of SPIE, 2007, vol. 6645, Article 66451J, pp. 1-10.

* cited by examiner

US 9,869,669 B2

BIOMARKER SENSING BASED ON NANOFLUIDIC AMPLIFICATION AND RESONANT OPTICAL DETECTION

RELATED APPLICATIONS

This application is a U.S. National Stage application of PCT/US2013/032519 filed Mar. 15, 2013, which claims priority from U.S. Provisional Patent Application Ser. No. 61/643,828 tiled May 7, 2012, which are hereby incorporated by reference in their entirety.

GOVERNMENT SUPPORT STATEMENT

This invention was made with government support under NSF Grant No. CTS0404124 awarded by the National Science Foundation. The government has certain rights in the invention.

FIELD OF THE INVENTION

This invention relates generally to the field of biomarker sensing, particularly a sensor platform to detect biomarkers, and specifically to the field of compact, lab-on-a-chip sensor platforms for detecting multiple cardiac biomarkers from microliter blood samples.

BACKGROUND OF THE INVENTION

Over 1.2 million new and recurrent heart attacks are diagnosed in the US every year. More than 500,000 of these patients will die within a year and, of these, about half will die within 1 hour of the appearance of symptoms. While emergency medical technicians, paramedics, and emergency room physicians could begin treating cardiac arrhythmias that are diagnosed in the first, "golden" hour following a heart attack, most people ignore symptoms for more than 2 hours and many delay treatment for more than 12 hours.

Lateral flow immunoassay (LFIA) is a point-of-care diagnostic platform, also known as immuno-chromatography or a dipstick assay. In LFIA, an analyte is absorbed through a membrane strip typically made of nitrocellulose, is labeled with recognition elements, e.g., immuno-labeled nanoparticles, and binds to immobilized anti-analyte lines sprayed on the strip. LFIAs are commercially available for various cardiac biomarkers, e.g., INSTANT-VIEW™ and NANO-CHECK™, and the reported limit of detection is on the order of 0.1 ng/ml for cardiac troponin-I (cTnI), 20 ng/ml for myoglobin (Myo), 2 nM/ml for creatine kinase MB (CK-MB), and 0.035 pg/ml for erythropoietin (EPO).

However, LFIA has a few disadvantages. For example, LIFA is not amenable to quantitative, precise, continuous, high-throughput analysis. When continuous (or periodic), quantitative diagnostic monitoring is desired for prognosis of heart problems, alternative means of detection may be needed.

Another platform is enzyme-linked immunosorbant assay (ELISA) where antibodies to cardiac biomarkers are immobilized microliter wells, and antibody-biomarker binding event translates to a detectable fluorescence signal. Although quantitative, conventional ELISA suffers from relatively long analysis time and high consumption of samples and reagents. Microfluidic immunoassay devices have emerged to address some of these issues. Today, commercial ELISA kits, e.g., those available from Abnova Corporation and Oxis International, Inc., are available for cardiac biomarkers, and the detectable range is on the order of 1-75 ng/ml for cTnI, 5-1000 ng/ml for Myo, 0.1-100 µg/ml for C-reactive protein (CRP), and 2.5-200 ng/ml for CK-MB.

What is needed in the art, therefore, is a platform that can provide rapid, point-of-care such as analysis of blood samples that overcomes the size and power limitations of conventional platforms where a large number of sensors are required for parallel processing. An accurate, portable and fast biomarker diagnostic would facilitate field diagnoses and would also allow on-the-spot detection of coronary disease during routine clinical visits.

SUMMARY

Embodiments described herein address many of the limitations mentioned above in regards to, for example, LFIA and ELISA, while providing quantitative, fast, high-throughput, label-free, highly targeted detection of sub-ng/ml concentrations of cardiac biomarkers. An advantage provided by at least one embodiment is lessening the need for highly skilled laboratory personnel with a complete understanding of the applicable procedures.

In an embodiment, there is a sensor platform that includes a substrate, a plurality of nanochannels disposed on the substrate, a plurality of electrodes, each electrode extending substantially across a width of the plurality of nanochannels, a waveguide disposed on the substrate and an analysis chamber and a reference chamber disposed on the substrate. The platform further includes at least one analysis optical resonator disposed in the analysis chamber and optically coupled to at least a portion of the waveguide, the at least one analysis optical resonator in fluid communication with at least one of the plurality of nanochannels, and at least one reference optical resonator disposed in the reference chamber and optically coupled to at least a portion of the waveguide, the at least one reference optical resonator in fluid communication with at least one other of the plurality of nanochannels.

In another embodiment there is a lab-on-a-chip platform system. The lab-on-a-chip platform system includes a substrate, a plurality of nanochannels disposed on the substrate, a plurality of electrodes, each electrode extending substantially across a width of the plurality of nanochannels, a waveguide disposed on the substrate, and an analysis chamber and a reference chamber disposed on the substrate. The lab-on-a-chip platform system further includes at least one analysis optical resonator disposed in the analysis chamber and optically coupled to at least a portion of the waveguide, the at least one analysis optical resonator in fluid communication with at least one of the plurality of nanochannels, and at least one reference optical resonator disposed in the reference chamber and optically coupled to at least a portion of the waveguide, the at least one reference optical resonator in fluid communication with at least one other of the plurality of nanochannels. The lab-on-a-chip platform system further includes an optical input source for providing an electromagnetic energy input to the waveguide, at least one photodetector for receiving an electromagnetic energy output from the waveguide, a processor in electronic communication with the at least one photodetector; and a controller in electronic communication with the processor, the optical input source, and an electrode potential source, the electrode potential source in electronic in communication with at least one of the plurality of electrodes.

In yet another embodiment, there is an integrated, lab-on-a-chip biosensor, that includes a preconcentrator stage and a resonant optofluidic detection stage fluidically coupled to the preconcentrator stage. The preconcentrator stage and the resonant optofluidic detection stage can both be located on the same substrate.

In even yet another embodiment, there is a method for detecting biomarkers in a sample of analyte fluid. The method includes providing a sample of analyte fluid to a integrated lab-on-a-chip biosensor, wherein the biosensor includes: a preconcentrator stage and a resonant optofluidic detection stage fluidically coupled to the preconcentrator stage. The method further includes preconcentrating the sample in the preconcentrator stage, providing the preconcentrated sample to the resonant optofluidic detection stage, detecting an output electromagnetic energy, and determining a concentration of one or more biomarkers in the analyte sample based on a characteristic of the detected output electromagnetic energy.

At least one embodiment described herein can facilitate real-time monitoring of cardiac biomarkers, for example, by providing the ability to track their concentration in a compact device. By providing quantitative analysis and evaluation of cardiac biomarkers, at least one embodiment can provide a benefit to both patients suffering from heart disease as well as those who are at potential risk of developing heart disease. Embodiments of a sensor platform described herein can also be highly versatile and transferrable to other trace biomarkers of medical importance. One benefit of at least one embodiment is a fully automated device that can be used with minimal training and without the need for bulky and expensive supporting equipment.

At least one embodiment provides a compact, lab-on-a-chip sensor platform to detect multiple cardiac biomarkers from microliter bloods samples.

At least one embodiment provides a fabrication method for integrating high-Q optical microresonators and FET nanochannels on a single chip. At least one embodiment provides a combination of these two technologies for an optofluidic and lab-on-a-chip platform capable of dynamic separation, amplification, and sensing.

In at least one embodiment there is a rapid point-of-care platform for myocardial disease that includes resonant optical detection of multiple cardiac biomarkers and advanced pre-processing to pre-concentrate and purify trace biomarkers before delivering them to an integrated optofluidic detector.

Additional advantages of the embodiments will be set forth in part in the description which follows, and in part will be understood from the description, or may be learned by practice of the invention. The advantages will be realized and attained by means of the elements and combinations particularly pointed out in the appended claims.

Further advantages of embodiments described herein include signal processing protocols and control algorithms that can be used in a variety of fluidic sensing systems where controlled flow rate and concentration are synchronized with the detection element to optimize the sensitivity for a specific target.

Other advantages of embodiments described herein include a compact sensor that utilizes low power consumption combined with a low volume of analyte consumed for diagnosis.

It is to be understood that both the foregoing general description and the following detailed description are exemplary and explanatory only and are not restrictive of the invention, as claimed.

The accompanying drawings, which are incorporated in and constitute a part of this specification, illustrate embodiments of the invention and together with the description, serve to explain the principles of the invention.

BRIEF DESCRIPTION OF THE DRAWINGS

FIG. 4a-4l illustrate stages of fabrication of the sensor platform chip such as that illustrated in FIG. 1a.

DESCRIPTION OF THE EMBODIMENTS

Reference will now be made in detail to the present embodiments, examples of which are illustrated in the accompanying drawings. Wherever possible, the same reference numbers will be used throughout the drawings to refer to the same or like parts.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less that 10" can assume negative values, e.g. −1, −2, −3, −10, −20, −30, etc.

The following embodiments are described for illustrative purposes only with reference to the figures. Those of skill in the art will appreciate that the following description is exemplary in nature, and that various modifications to the parameters set forth herein could be made without departing from the scope of the present invention. It is intended that the specification and examples be considered as examples only. The various embodiments are not necessarily mutually exclusive, as some embodiments can be combined with one or more other embodiments to form new embodiments.

While the below descriptions provide details of certain embodiments, they do not limit other embodiments from using other suitable methods or materials. Those of skill in the art will appreciate that the following description includes, but is not limited to, preferred and/or example embodiments of the present invention. Certain embodiments of the present invention are described by the appended claims.

Figure 1A:
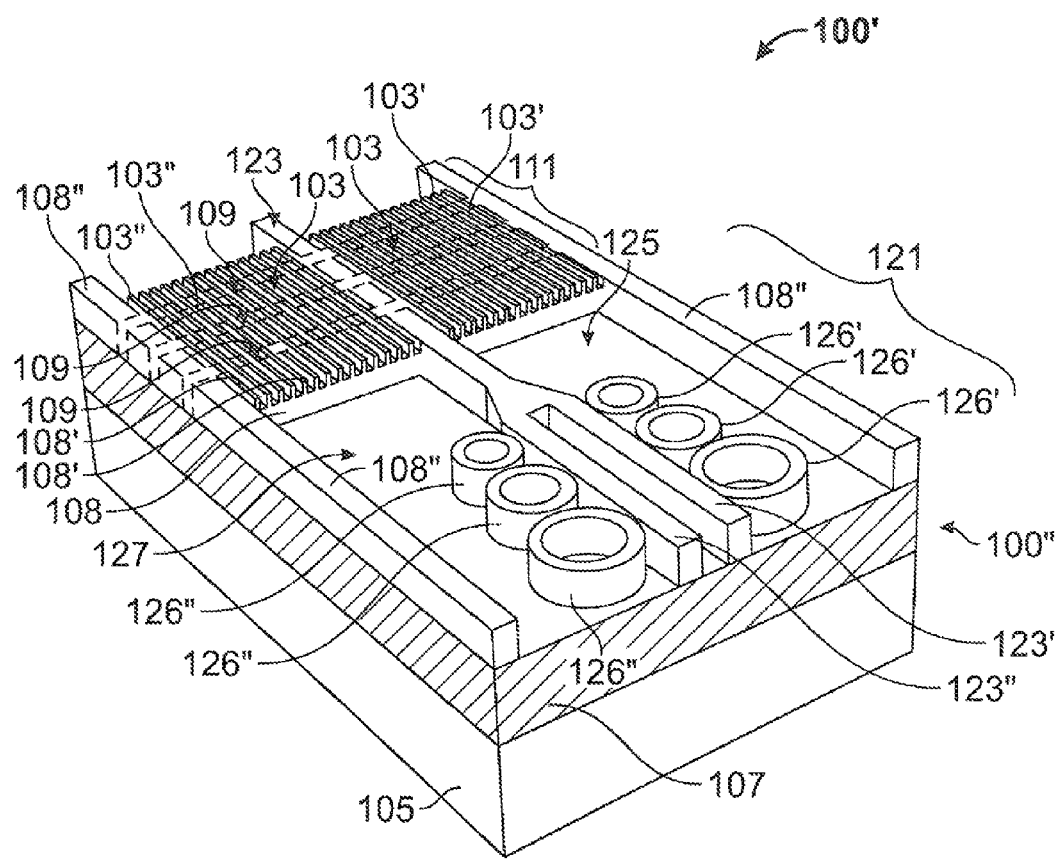
FIG. 1a is schematic representation of a sensor platform of an embodiment.

As shown in FIG. 1a, a lab-on-a-chip sensor platform 100' includes a nanofluidic field effect transducer (FET) separation/amplification section 111 and a resonant optical detection section 121 formed on a surface of at least one layer of a substrate 100", for example on at least one layer of a SOI substrate. The separation/amplification section 111 acts as a preconcentrator stage and section 121 acts as a resonant optofluidic detection stage being fluidically coupled to the preconcentrator stage 111.

The nanofluidic FET separation and amplification section 111 can include a nanochannel array 103, for example a gated nanochannel array, that includes at least one nanochannel, for example a plurality of nanochannels. In an example, the nanochannels array 103 includes at least one nanochannel 103' and at least one nanochannel and 103". A bottom portion (not visible) of the at least one nanochannel can be formed of at least a portion, such as an etched-down surface portion, of a top layer of the substrate 100", for example of top layer 108 which can be a silicon layer of an SOI substrate 105/107/108. In another example, a bottom portion of the nanochannels can be formed as a layer deposited on the substrate 100". Each nanochannels, for example the at least one nanochannels 103' and the at least one nanochannel 103" of the nanochannel array 103, can also be defined by nanochannel sidewalls 108' which can be formed by removing a portion of the substrate 100", such as via etching a portion of the top layer 108 of the substrate 100". In an example, the nanochannels sidewalls can be formed by depositing a material over the substrate 100", such as over the top layer 108. The nanochannels 103' and 103" can share similar characteristics. For example, the nanochannels can have a depth up to about 400 nm. Additionally, the nanochannels can have a width defined by a distance between two adjacent nanochannels sidewalls 108' of about 10 nm to about 1 µm.

Figure 1B:
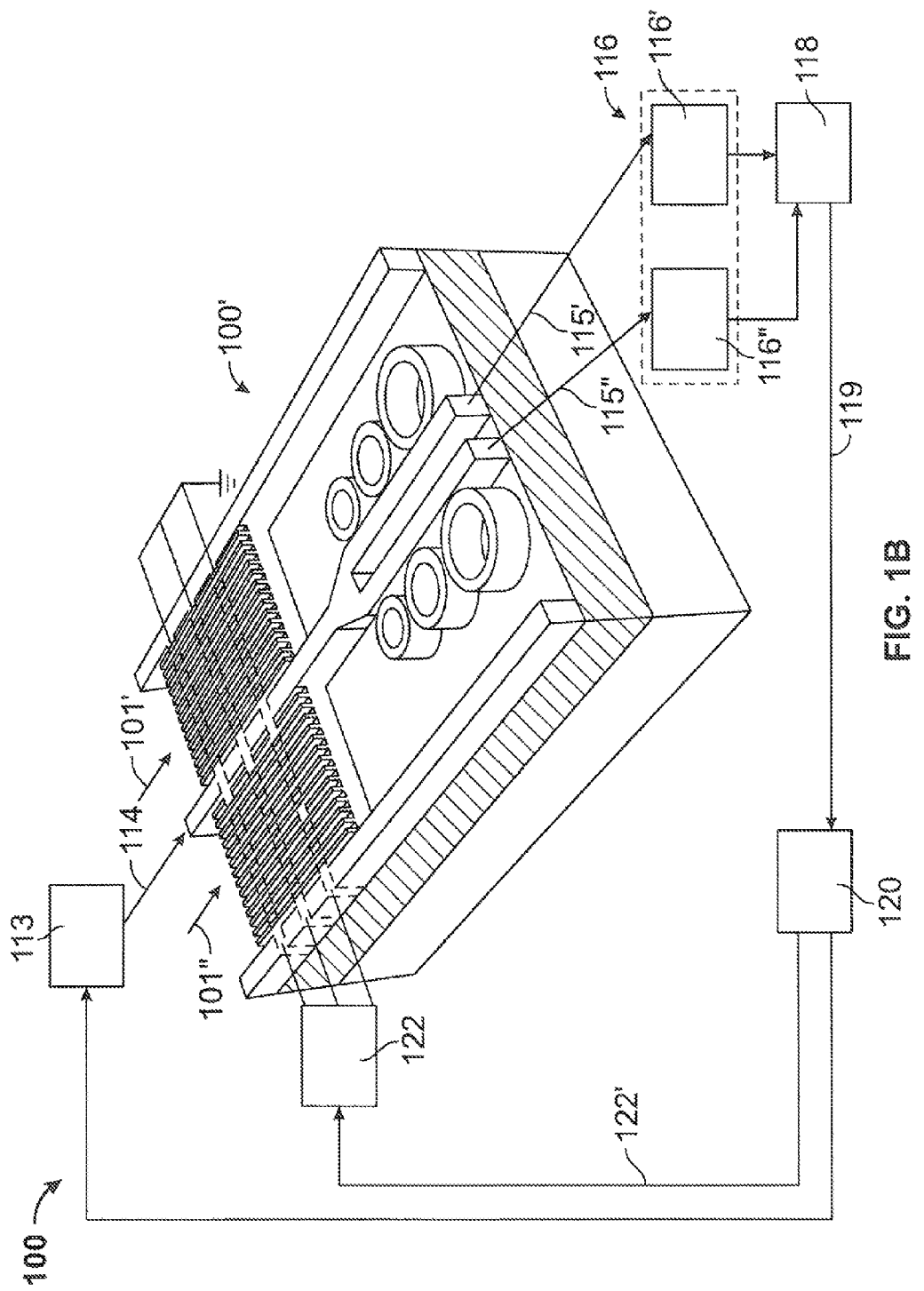
FIG. 1b is a schematic representation of a sensor platform system of an embodiment, including the sensor platform of FIG. 1a FIG. 1c shows the sensor platform of FIG. 1a with an insulating layer formed over the top surfaces of the microrings, waveguides, nanochannels array and chamber sidewalls.

The FET separation and amplification section 111 can include at least one electrode 109, such as a plurality of electrode. The at least one electrode can be formed as a gate, that is, a doped portion of layer 108. P-type or n-type dopant can be used for doping at least a portion of layer 108 to form gate electrode 109. In such an example, p-type or n-type dopant such as boron or phosphorous, respectively, can be used to dope a silicon layer as layer 108 of an SOI substrate as substrate 100", thereby forming a highly doped ($10^{19}$-$10^{21}/cm^3$) silicon layer as the at least one gate 109. Gate 109 can be formed by providing dopant to layer 108 by ion-implantation or by depositing a dopant-source layer over a mask formed over layer 108 and allowing dopant to diffuse out of the dopant-source layer and through non-masked portions into layer 108. The at least one gate 109 can be in electrical communication with a gate potential source 122 as shown in FIG. 1b. The gate potential source 122 can be configured to control a gate voltage of the at least one gate 109.

Returning to FIG. 1a, an optical waveguide 123, such as an Si optical waveguide, can extend across a surface of the lab-on-a-chip sensor platform chip 100'. For example, optical waveguide 123 can extend from a side of a surface of the platform, at least partially through the nanofluidic FET separation and amplification section 111, and at least partially through the resonant optical detection section 121. Optical waveguide 123 can be formed via patterning of the top layer 108 of substrate 100". The optical waveguide 123 can be configured as in a y-shape to include two waveguides 123' and 123". The waveguides 123' and 123' can be, for example, two, single-mode, Si optical waveguides. In other words, the waveguide 123 can include a first portion with the at least one nanochannel 103' formed on one side thereof, and at least one nanochannel 103" formed on another side thereof. The waveguide can include a second portion extending through at least a portion of the resonant optical detection section 121. The second portion of the waveguide can include a first leg (forming optical waveguide 123') and a second leg (forming optical waveguide 123"). In an embodiment, optical waveguides 123' and 123" can be formed substantially parallel to one another and extend across at least a portion of the resonant optical detection section 121. Optical waveguide 123 can divide the chip 100' between an analysis chamber 125 and a reference chamber 127.

Analysis chamber 125 and reference chamber 127 can be formed, for example with waveguide 123 formed between them, to prevent fluidic communication between the two chambers. Analysis chamber 125 can be configured such that a surface of analysis optical resonators 126' receive flowable medium, such as an analysis portion of the analyte sample such as a concentrated analysis analyte solution exiting from the at least one nanochannel 103' from the FET section 111. Reference chamber 127 can be configured such that a surface of reference optical resonators 126' receive flowable medium, such as a reference portion of the analyte sample such as a concentrated reference analyte solution exiting from the at least one nanochannels 103" from the FET section 111. To prevent spillage of flowable medium over an edge of the substrate 100", sidewalls 108" and 108" can be formed on a surface of the substrate. Sidewalls 108' and 108" can extend from at least a portion of the separation and amplification section through at least a portion of the resonant optical detection section 121. In an example, sidewalls 108' and 108" are formed from patterned layer 108 of substrate 100", such as the silicon layer of an SOI substrate. In another example, sidewalls 108' and 108" can be formed by depositing a material onto a surface of substrate 100".

Optical waveguides 123' and 123" can each be optically coupled to at least one of a respective immunodiagnostic sensor/detector. The immunodiagnostic sensor/detector can include at least one optical resonator, for example, at least one optical microring resonantor. That is, at least a portion of optical waveguide 123 such as optical waveguide 123' can be optically coupled to at least one of an analysis optical microring resonator 126' of the reference chamber 125. Optical waveguide 123" can be optically coupled to at least one of a reference optical microring resonator 126" of the reference chamber 127. To provide optical coupling of light between the waveguide and the optical resonators, the at least one analysis optical resonator 126' and the at least one reference optical resonator 126" can each be disposed between about 100 nm to about 300 nm from a respective sidewall of waveguide 123' and waveguide 123", respectively. The at least one optical microring resonator 126' and/or the at least one optical microring resonator 126" can be disposed on a surface of the substrate 100'. In an example, the at least one optical microring resonator 126' and/or the at least one optical microring resonator 126" can be formed by patterning a layer such as layer 108 of substrate 100". Accordingly, the at least one analysis optical microring resonator 126' and the at least one reference optical microring resonator 126" can each be formed as a high-Q Si optical microring resonator patterned out of a portion of the Si top layer of the SOI substrate.

In an example, the at least one analysis optical microring resonator 126' and the at least one reference optical microring resonator 126" can be substantially identical. For example, the at least one analysis optical microring resonator 126' and the at least one reference optical microring resonator 126" can be formed substantially of the same materials, sizes and shapes, except that in an example, at least a portion of the at least one reference optical microring resonator 126" can be coated. In other words, to achieve a high specificity of the sensor, at least a portion of a surface of the at least one analysis optical resonator 126' can be coated with at least one antibody that has a strong affinity for at least one target molecule type. In an example, a surface of the at least one analysis optical resonator 126' can be coated with at least one antibody such that a binding of at least one target molecule type to the coated surface causes a shift in a resonance wavelength of the at least one analysis optical resonator. That is, at least a portion of the surface of the at least one analysis optical microring resonator 126' in the analysis chamber 125 can be functionalized with antibodies. In an example, at least a portion of the surface of the at least one analysis optical microring resonator 126' can be functionalized with an antibody and the at least one reference optical microring resonator 126" is not functionalized with an antibody.

In an example, at least a portion of a first analysis optical microring resonator can be functionalized with at least a first type of antibody, and at least a portion of the surface of a second analysis optical microring resonator can be functionalized with a second antibody that is different than the first antibody. In an example, the at least one reference optical microring resonator 126' includes three micro-rings, such as a first, second and third microring, disposed in the analysis chamber 125 to simultaneously detect cardiac troponin-I (cTnI), myoglobin (Myo) and creatine kinase MB (CK-MB). In other words, for highly specific immuno-binding, a surface of each of the analysis optical microring resonator can be functionalized with a respective one antibody that can bind to a specific cardiac biomarker. For example, the, i.e., cTnI, Myo and CK-MB, respectively.

As shown in FIG. 1b, the lab-on-a-chip sensor platform system 100 can include chip 100 in optical communication with at least one photodetector 116, such as analysis photodetector 116' and reference photodetector 116". The at least one photodetector 116 can receive output electromagnetic energy 115 (such as 115' and 115") from chip 100'. The at least one photodector 116 can be in communication with a processor 118. Processor 118 can be in communication with a controller 120. And controller 120 can be in communication 122' with potential source 122 as well as an optical input source 113. Optical input source 113 can be, for example, a tunable laser. Optical input source 113 and can be in optical communication for providing input electromagnetic energy 114 to the chip 100'.

The lab-on-a-chip sensor platform 100 described above can be configured to pre-process a sample, for example a finger stick blood sample, in order to isolate target biomarkers, concentrate them by at least 3-4 orders of magnitude in the FET section 111 and deliver them to the at least one microring detector in section 121 in less than about 10 minutes.

Analyte sample can be provided to lab-on-a-chip sensor platform 100, and separated as indicated by arrow 101' and 101" in FIG. 1b into the analysis chamber 125 and reference chamber 127, respectively. Pre-processing of the sample to isolate target biomarkers can be carried out in the nanofluidic FET separation and amplification section 111. For example, nanofluidic FET separation and amplification section 111 can utilize a dynamic electric field gradient to capture, and then deliver target biomarkers from the sample to the resonant optical detection section 121. The dynamic electric field gradient can be formed in an electric-field extending between gates 109. For example, a different potential can be applied to each of the at least one gate 109 by potential source 122 to locally control a surface charge, $\zeta$-potential, and pH adjacent to each of the at least one gate, rendering a desired longitudinal potential gradient and a pH gradient along the nanochannels of the nanochannels array 103. This real-time control can provide for dynamic separation/amplification. Accordingly, the desired markers in the analyte can be separated and focused through the nanofluidic FET section and eluted downstream towards the resonant optical detection section 121 and the at least one optical microring resonator therein.

As discussed above, the analyte can be divided between the analysis chamber 125 and the reference chamber 125. Target molecules in the analyte sample, therefore, can bind to a antibody coating of the at least one optical microresonator in the analysis chamber. Such binding events, as explained below, can cause a shift of the resonance frequency of the at least one optical resonator in the analysis chamber. However, in embodiments in which the optical resonators of the reference chamber are not coated with such antibodies, such binding events as in the analysis chamber will not occur, and thus any change in resonance of the reference optical resonators will not be due to binding events. As a result, a comparison can be made between changes in resonance of the optical resonators in the analysis chamber caused by binding events to calculate concentration of target molecules in the analyte. Changes in resonance not due to binding events (such as those caused by temperature variation) can be accounted for by tracking the change in resonance, if any, in the reference optical resonators.

For example, optical input source 113 can provide electromagnetic energy 114, such as laser light at an optical input power of 1-5 mW, to the optical waveguide 123. The electromagnetic energy provided to the optical waveguide 123 can be divided between optical waveguide 123' and optical waveguide 123". As target molecules are focused through nanochannels 103' of the nanofluidic FET section and eluted, they are delivered into the analysis chamber 125'. In the analysis chamber, the target molecules can bind to a corresponding antibody coated on the at least one optical microresonator 126'. As a result, an effective refractive index of the resonant optical mode thereof can change. These binding events can be translated to an optical resonant wavelength shift. And, due to the high optical quality factor of the at least one optical microresonators 126, very small resonant shifts (caused by a small number of occupied binding sites) can be measured, resulting in very high sensitivities of measurements. Accordingly, utilizing a plurality of micro-rings that have at least a portion of their surfaces functionalized with different antibodies, a concentration of different biomarkers can be simultaneously determined in parallel on a single chip, such as in system 100. In other words, while not intended to be limited by any particular theory, it is believed that as the biomarkers bind to the at least one functionalized ring 126' (in the analysis chamber 125), the resonant wavelength shifts in proportion to the number of biomarker molecules that bind to the rings 126'.

An optical output 115' from the analysis chamber 125 can be registered by at least one photodetector, such as analysis photodetector 116'. Analysis photodetector 116' can, therefore, generate an analysis signal 117' that is representative of characteristics of the analysis optical output 115', such as a change in a resonance frequency. Analysis signal 117' can be received by a processor 118 in communication with the analysis photodetector 116'. Processor 118 can convert the analysis signal 117' into at least one value representative of a measurement of the magnitude of the resonant wavelength shift of each of the at least one ring 126'.

For example, as the optical source 113 (e.g., tunable laser) provides input light 114 at varying wavelengths (i.e., optical source 113 performs sweeps across a range of frequencies) to waveguide 123, and waveguides 123' and 123", the light interacts with optical ring resonators 126' and 126". As target molecules from an analyte sample bind to rings 126', a resonance wavelength of the at least one ring 126' shifts to another resonance frequency. The photodetectors 116' and 116" analyze output light 115' and 115" exiting waveguides 123' and 123", respectively. As a result, photodetectors 116' and 116" produce an output signal 117' and 117" which is provided to processor 118. Processor 118 can analyze the signals 117' and 117" to determine resonance wavelength of the rings 126' and 126" during a particular sweep. As the resonance wavelength shifts, processor 118 can calculate a resonant wavelength shift to calculate a concentration of at least one biomarker in the sample. Any shifts in resonance wavelength attributable to other conditions aside from binding events can be determined from wavelength shifts determined from output light 116" based on changes in resonance wavelength of rings 126" affected by the reference portion of the analyte sample.

In other words, an optical output signal 115" of the reference chamber 127 can be registered by the at least one photodetector, such as reference photodetector 116". Reference photodetector 116", therefore, can generate a reference signal 117", representative of characteristics of the reference optical output 115". Reference signal 117" can be received by processor 118 in communication with reference photodetector 117". Processor 118 can translate the reference signal 117" into at least one value representative of the magnitude of the resonance of each of the at least one ring 126", for example, as the optical source 113 (e.g., laser) wavelength is swept across a range of frequencies.

Utilizing differential sensing, the lab-on-a-chip platform system 100 can enhance a signal-to-noise ratio by eliminating the wavelength shifts not associated with the biomarker binding events that occur in analysis chamber 125. For example, processor 118 can compare values assigned to the characteristics of the output electromagnetic energy 115' representative of the magnitude of a resonance wavelength shift of each ring 126' with values assigned to the characteristics of the output electromagnetic energy 115" representative of the magnitude of the resonance wavelength of each ring 126". In other words, the concentration of each biomarker from an analyte sample can be evaluated from the resonant shift of the at least one ring 126' functionalized with the corresponding antibody as target molecules from the analyte sample bind to a corresponding antibody. Processor 118 can thereby generate a signal, such as processed differential signal 119, which can be communicated to a controller 120 that is in communication with the processor. Utilizing the signal 119 in a feedback control loop, the controller, in communication with optical input source 113 and gate potential source 122, can adjust the gate potentials (Vg) provided by the gate potential source to gates 109 as well as the optical input wavelength of the electromagnetic energy 114 provided by the optical input source 113 for maintaining optical detection.

As described above, therefore, in an example, an integrated sensor includes two technologies on a single chip to detect ultra-low concentrations of biomarkers with high sensitivity. In an embodiment, the FETs in FET section comprising the nanochannels and gates can be used to amplify the concentration of targeted biomarkers by a factor of $10^3$-$10^4$ or more. Low-loss optical microring resonators can be used in the detection of biomarkers at concentrations as low as 1-10 ng/mL, resulting in a combined limit-of-detection of 0.1-10 pg/mL.

Figure 1C:
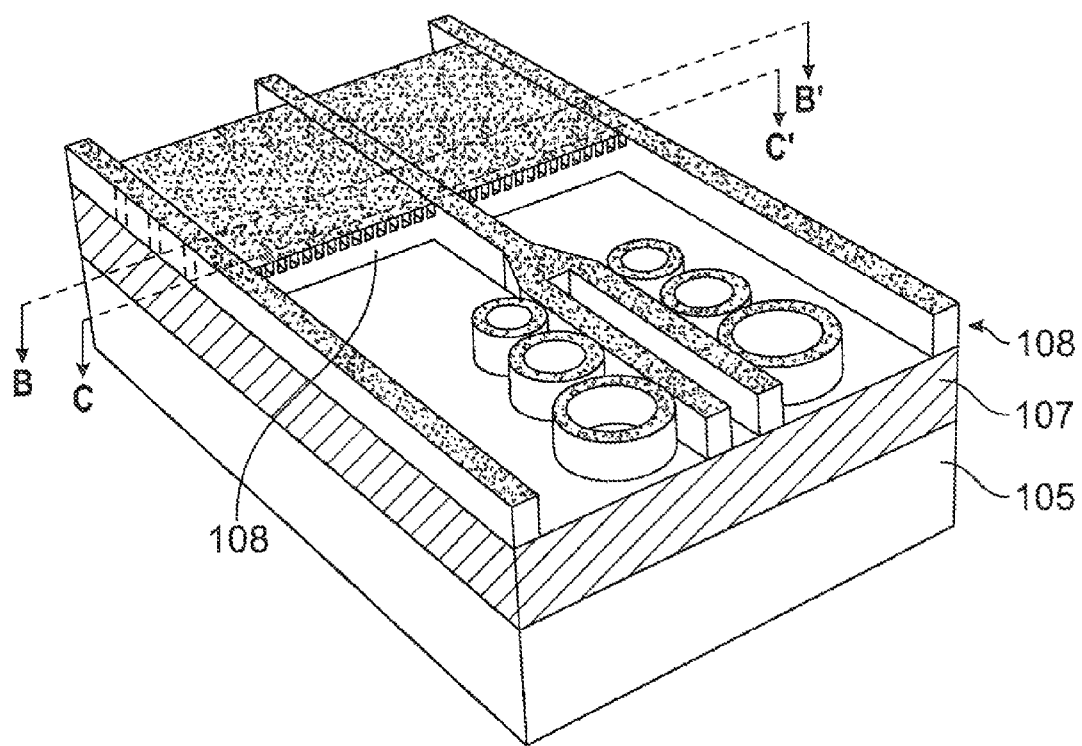
FIGS. 1d-1e show cross sectional views of portions of FIG. 1c.
Figure 1D:
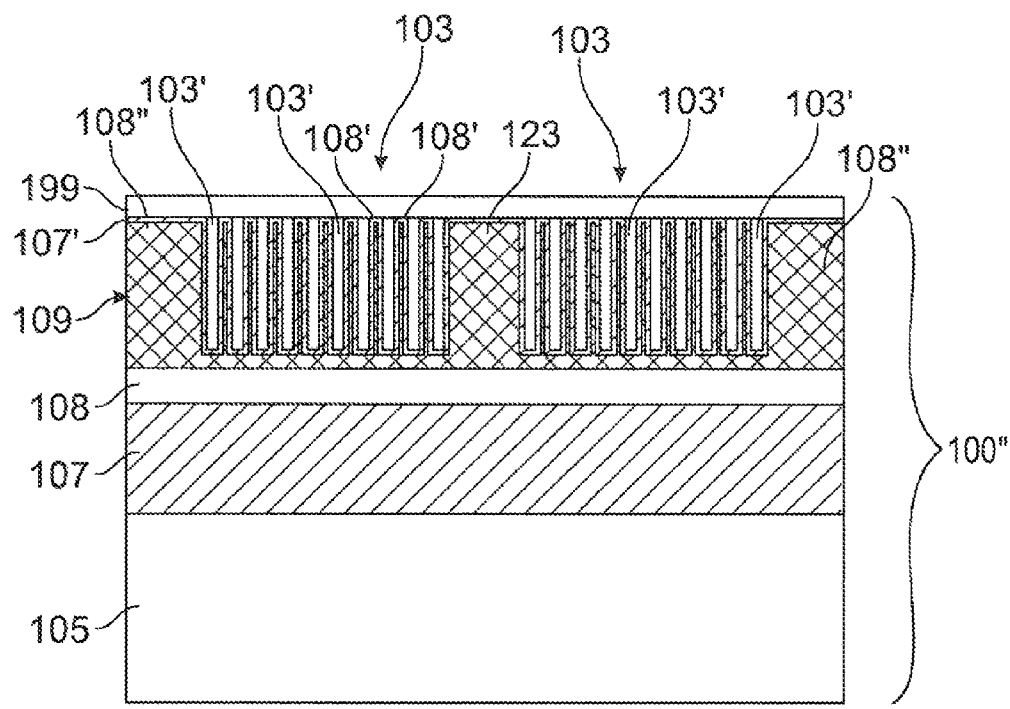
Figure 1E:
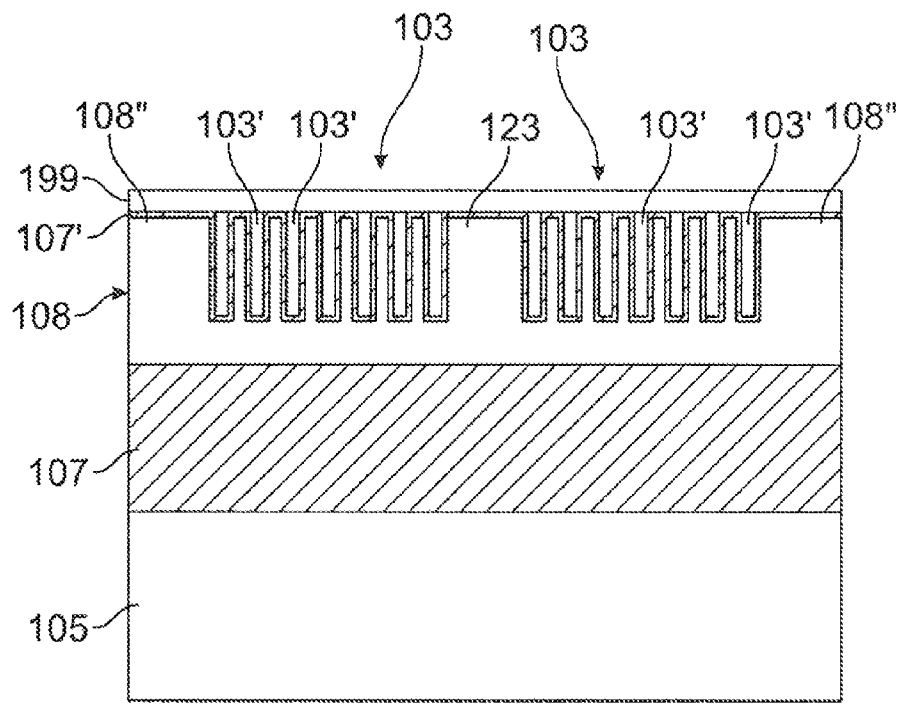

Returning briefly to FIG. 1a, a top surface of the microrings 126' and 126", waveguides 123, 123' and 123", nanochannels arrays such as at nanochannel sidewalls 108' and the chamber sidewalls 108" can be oxidized, such as thermally oxidized, to form an oxidized layer 107" thereon as shown in FIGS. 1c-1e. In other words, as described above, the microrings 126' and 126", waveguides 123, 123' and 123", nanochannel sidewalls 108' and chamber sidewalls 108" can be formed by patterning layer 108 of substrate 100". These features, therefore, can be formed of the same material as layer 108. That is, as shown in FIG. 1e, waveguide 123, nanochannel sidewalls 108' and the chamber sidewalls 108" are shown as being formed from layer 108. FIG. 1d similarly shows that these features can be formed as the doped portions of layer 108 that form the at least one gate 109. In FIGS. 1d-e, insulating layer 107', such as an $SiO_2$ layer formed by thermal oxidation of layer 108, is shown at a top surface of layer 108 and the at least one gate 109, respectively. An additional layer 199 can be formed via, for example, anodizing Detection with Optical Microring Resonators.

The resonators can be optical resonators, such as optical ring resonators, such as optical microring (or micro-ring) resonators 126' and 126". The optical microring resonators can be micron-size ring-shaped dielectric optical cavities that can confine and store optical energy in a small volume (~50 μm$^3$) within a limited bandwidth around discrete resonant wavelengths associated with each optical mode. In an example, the at least one optical resonators can be at least one microsphere optical resonators that are substantially spherical instead of being ring shaped. A surface of the at least one microsphere optical resonators can be coated with at least one antibody. In an example, the at least one optical resonators can include at least one optical microring resonator and at at least one microsphere optical resonator.

Figure 2A:
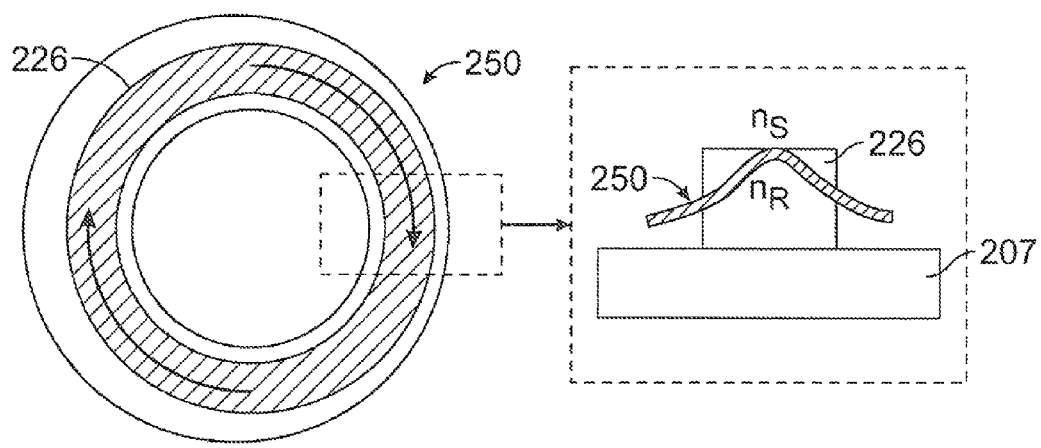
FIG. 2a provides a top-view (left side of figure) and cross-sectional view (right side of figure) of a representation of an optical microresonator showing an "evanescent" optical field extended in the surrounding medium.

Optical energy provided to the optical resonators, for example via waveguides in optical communication therewith, can be confined and guided inside the ring structure of an individual microring, by means of total internal reflection (as indicated by the arrows within optical resonator of FIG. 2a). Accordingly, the refractive index of the ring ($n_R$) should be larger than that of the surrounding medium ($n_S$). As illustrated in FIG. 2a, although the optical field can mainly be confined inside the microring 226, there can be an evanescent field 250 that extends beyond the ring boundary into the surrounding medium. It is through the evanescent field 250 that the effective refractive index ($n_{eff}$) of each optical mode ($n_S < n_{eff} < n_R$) is affected by $n_S$ and therefore by the presence of molecules in the vicinity of the optical resonator, such as the target molecules present in a sample, such as a analyte sample from blood, which can bind to antibodies coated on the optical resonator. The resonant wavelength of each optical mode ($\lambda_{res}$) is proportional to $R \times n_{eff}$, where R is the radius of the ring, so any change in the optical properties of the medium produces a resonant shift, $\lambda_{res}$, through $n_{eff}$:

$$\delta\lambda_{res} = \lambda_{res} \times \frac{\delta n_{eff}}{n_{eff}}. \qquad (1)$$

Not intending to be limited to any particular theory, it is believed that the presence of any particle or molecule in the vicinity of the ring affects $n_{eff}$, and therefore, the resonant optical wavelength of the at least one optical resonator, through two types of interaction between molecules and the evanescent field: absorption and polarization. Absorption of optical energy by a molecule creates a local temperature gradient and modifies $n_{eff}$ through the thermo-optical effect, $\Delta n_{eff} = (dn/dT) \times \Delta T$. Polarization of a molecule by the evanescent optical field results in a modified refractive index in the vicinity of the molecule according to: $n_S^2 = 1 + P/\epsilon_0 E$, where P is the polarization and E is the optical E-field.

Figure 2B:
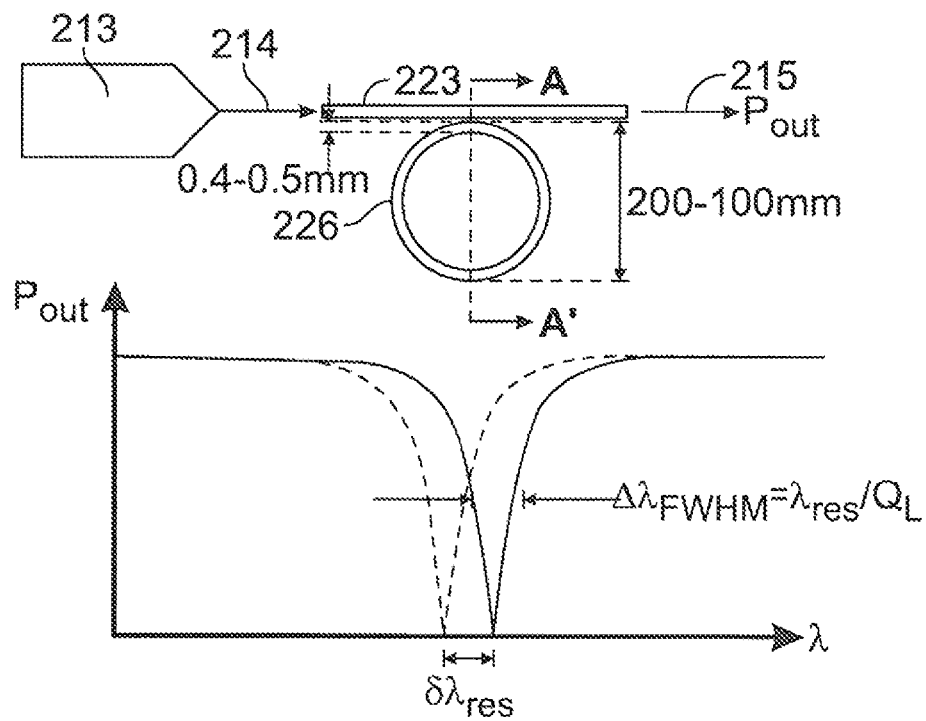
FIG. 2b illustrates the function of a waveguide-coupled optical microring resonator (upper portion of the figure) and a graph (lower portion of the figure) illustrating the corresponding spectrum of transmitted optical power.

The resonant shift can be dominated by polarization effect unless the optical power of the electromagnetic energy "circulating" in the ring is very large, or the resonant wavelength matches one of the absorption lines of the molecules. The spectral shape of resonant optical power in the vicinity of resonant wavelengths ($\lambda_{res}$) has a Lorentzian shape with a full-width-half-max ($\Delta\lambda_{FWHM}$) that is inversely proportional to the optical quality factor of the optical cavity. As shown in FIG. 2b, the resonant wavelength ($\lambda_{res}$) shift can be measured by optically coupling the microring 226 to an optical waveguide 223. That is, input electromagnetic energy 214 produced by a source 213, such as a laser, can be provided to the optical waveguide 223. The electromagnetic energy can be provided over a range of wavelengths, including a resonance wavelength. The optical power ($P_{out}$) of the transmitted output 215 can be monitored, for example, by photodetectors as described above.

In order to bind target molecules on the optical ring resonator, the surface of the ring can be functionalized with monoclonal antibodies that selectively bind the target molecules to the surface of the ring. While not limited by a particular theory, the polarization effect of a molecule layer on the surface of the ring can be shown to shift the resonant wavelength by:

$$\delta\lambda_{res} \propto \lambda_{res} \times \frac{\alpha_{ext}\sigma}{\epsilon_0(n_R^2 - n_S^2)R}, \qquad (2)$$

where $\alpha_{ext}$ is the excess polarizability of the molecules binding to the surface, and σ is the average surface density of molecules. Depending on the measurement techniques and tools, and level of noise in the system, the minimum detectable resonant shift (with reasonable signal-to-noise ratio) is a fraction F of $\Delta\lambda_{FWHM}$. For a given F and device parameters, the minimum detectable molecule surface density ($\sigma_{min}$) can be written as:

$$\sigma_{min} = \frac{\epsilon_0 RF(n_R^2 - n_S^2)}{\alpha_{ext} Q_L}, \qquad (3)$$

It should be noted that, for protein molecules, $\alpha_{ext}$ is roughly proportional to the mass of the molecule.

Figure 2C:
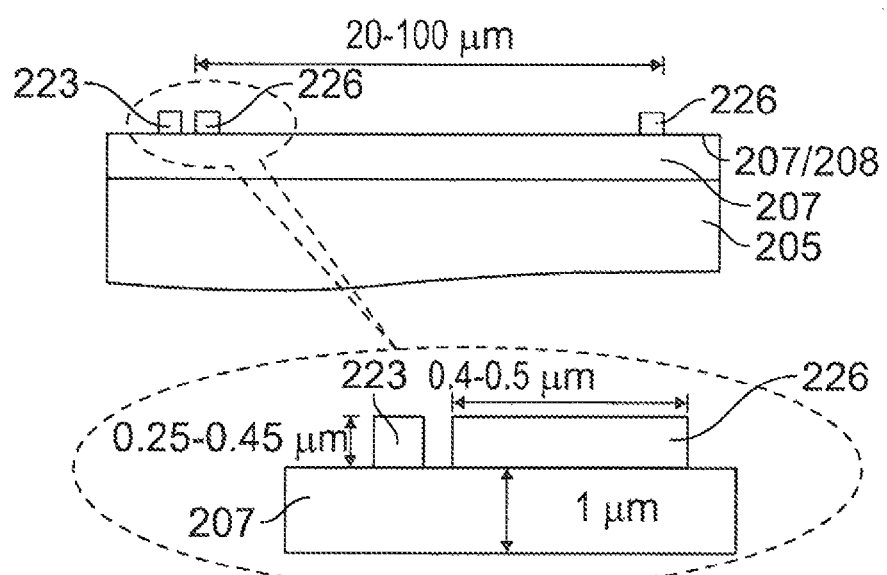
FIG. 2c provides a cross-sectional view of a silicon-on-insulator (SOI) optical microring resonator side-coupled to a SOI waveguide.

As described further below, both waveguide 223 and microring 226 can be fabricated on a SOI wafer 205/207/208. FIG. 2c shows a cross-sectional view taken at A-A' of FIG. 2b showing SOI optical microring resonator 226 and SOI waveguide 223.

Silicon-on-Insulator (SOI) Optical Microring Resonator

Monolithic optical microring resonators, such as optical microring resonators described in the various examples herein, can be fabricated using a variety of material systems. In an example, SOI microring resonators are formed due to their compatibility with the material system used to fabricate active separation nanochannels, such as those utilized in the nanofluidic FET separation and amplification section of FIG. 1a and described above. Moreover, a silicon-based optical resonator can be integrated with CMOS electronic circuits as control (such as controller 120) and signal processing (such as processor 118) units in the sensor. The optical-quality factor of SOI microring resonators include very high Q-factors, $>10^5$.

Optical Detection of Cardiac Biomarkers

Molecular polarization rather than absorption is relied upon as the main mode of optical detection. Most biomolecules have a relatively complex structure and a non-trivial absorption spectrum. Moreover the absorption spectrum of most proteins is in the UV regime and some vibrational absorption lines associated with the peptide bond. However, the high-Q operation of SOI micro-rings is limited to the near and mid-IR regime where most tunable lasers, detectors and optical components are readily available, i.e., near 1550 nm. In contrast, the polarization effect, also known as reactive interaction, is less sensitive to optical wavelength, and it is mainly sensitive to molecular mass (basically the optical polarization of each molecule in the evanescent field equally perturbs the effective refractive index). Therefore, for microresonators, the reactive interaction is the preferred mode of detection over commonly used absorption spectroscopy, and it is effective for detecting a wide variety of molecules. When reactive interaction is used, the specificity of the detection mechanism is solely provided through functionalization of the optical microresonator surface by an antibody (e.g., those associated with cardiac biomarkers). The total number of molecules that bind to the microring will be proportional to their concentration in the analyte. Hence, the magnitude of the resonant wavelength shift is proportional to the concentration of the corresponding molecule.

Multi-Ring Sensing

To detect the presence of multiple biomarkers simultaneously, at least one microring, preferably multiple optical microring resonators each with unequal diameters can be used. Each ring can be functionalized with the antibody associated with one of the target molecules. Because of their unequal diameters, the resonant wavelength of each microring is different and can be monitored independently by tuning the optical energy source such as a laser across various wavelengths. For example, the concentration of each molecule in the liquid surrounding the microring can be monitored as the laser wavelength is scanned through all resonant wavelengths. There are at least three proteins that can be considered as signature of injury: cardiac troponin-I (cTnI), myoglobin (Myo) and creatine kinase MB (CK-MB), so simultaneous monitoring of these proteins in the blood serum can improve the accuracy the diagnosis of myocardial injury.

Differential Sensing Scheme

The high sensitivity of the at least one optical microring resonator makes it susceptible to various external perturbations, e.g., thermal, vibrational, etc., that can be translated into false resonant shifts. Also, molecules other than the target molecules can non-specifically bind to the microring surface and cause error. To avoid these problems, a differential sensing scheme can be used where the analyte stream is divided between two chambers: an active chamber with at least one surface-functionalized micro-ring (i.e., active surface-functionalized microrings), and a reference chamber with at least one non-surface functionalized micro-ring (i.e., passive micro-rings). The resonance wavelength of the active micro-rings and the passive microrings and are monitored from optical power output exiting each of two separate waveguides. By subtracting the photocurrents generated by the transmitted optical power through each one of these waveguides, these external perturbation effects are eliminated, and only specific binding events associated with antibody-antigen binding on the active rings will be considered from the detected signal for use in determining the target molecule concentrations from the samples.

Ring Immunoaffinity Biosensor

The resonant wavelength of a high-Q optical micro-ring resonator can be extremely sensitive to the optical properties of the surrounding medium. If the surface of the ring is coated with an antibody, binding of target molecules shifts the resonant wavelength in direct proportion to the mass of analyte bound, resulting in a very sensitive detection. For a microring with very low optical losses, i.e., high optical quality or high-Q, this wavelength shift can be measured with high accuracy by monitoring the transmitted laser power through a waveguide optically coupled to the optical resonator. In an example, silicon optical microring resonators can be used as immunoaffinity sensors for simultaneous detection of several cardiac biomarkers. As such, a lab-on-a-chip platform as described herein can provide detection sensitivity down to 1 ng/ml.

Sample Purification and Concentration

Whole blood must be processed before target biomarkers can be delivered to the resonant optical detection section, in particular, to remove high-abundance interferents.

EXAMPLE 1

Pre-Processing in the NanoFluidic and FET Separation and Amplification Section

Pre-processing begins by loading a sample onto the chip, e.g., a 5 µL finger stick droplet of blood. To do this, a sample is first mixed with anti-coagulant buffer and is then introduced onto the chip. The sample is next flushed into a microchannel plenum, and the proteins pass into the nanochannels, which reject platelets and red or white blood cells due to their size. As this protein soup enters the nanochannels, the FET gate electrodes begin electrofocusing the target biomarkers to concentrate them while clearing contaminants.

The FET gate electrode voltages, buffer pH, ionic strength, and hydraulic flow are chosen so that most of the proteins are removed from the troponins in a few minutes, while they are captured and concentrated 1000-fold. In the case of the troponins, this is easily done since the cTnI's are very basic, $10.5<pI<11.5$. By choosing a running buffer with a $8<pH<9$, all of the neutral and acidic proteins will flush through the device, leaving a handful of basic proteins including the cTnI. By further setting an electric field gradient with a step change that captures primarily wild-type and phosphorylated troponins, many of the remaining basic proteins can also be eliminated before the troponins are delivered to the sensor rings.

The concentration of salts in whole blood is on the order of 150 mM and is primarily made up of strong electrolytes like sodium, magnesium and chloride which, if present, would interfere with preprocessing by depressing the electric field due to their high conductivity. However, since the electrofocusing step can remove salts contained in the sample, the net effect of the high salt concentration in the sample will be to slow down focusing while the salts are mobilized out of the separation channel. Under these operating conditions, the anions from the sample can simply pass through the nanochannel array but the small cations, which have a higher electrophoretic mobility than the troponins, will collect near the entrance to the array. If needed, the cations can be entirely removed from the array entrance by placing a remote electrode in a reservoir attached to the Inlet plenum.

After the high-abundance proteins, salts, and other interferents have been removed from the troponins in the sample, and once they have been concentrated into narrow, discrete peaks, the target biomarkers can be delivered one at a time to the sensors by eluting them with a moving electric field gradient and then passing them over the rings in a hydraulic flow.

EXAMPLE 2

Method of Manufacturing

The technologies used to fabricate the FET nanochannels and optical detectors can be complementary metal oxide semiconductor (CMOS) compatible, so the complete platform: nanofluidic separation, optofluidic detection and electronic analysis, can be fabricated on a single chip with a footprint of about $1\times4$ cm$^2$. Both nanofluidic FETs and optical microring resonators can be used for separation and label-free detection of biomolecules, respectively, and can be combined on the same platform, as described above. In an embodiment, sensitive (<1 ng/mL), fast (<10 minutes) and label-free detection of cardiac biomarkers, e.g., cardiac troponin-I (cTnI), myoglobin (Myo), and creatine kinase MB (CK-MB) can be achieved using a small volume, <5 µl, of blood serum. These markers are present in elevated concentrations in the bloodstream of a patient suffering from acute myocardial infarction and their early detection is an important part of the diagnostic process.

EXAMPLE 2A

Fabrication of an Optical Resonator and Optically Coupled Waveguide

Figure 3A:
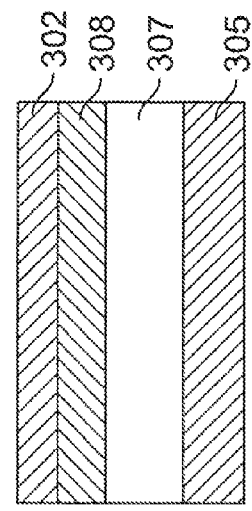
FIG. 3a-3e illustrates stages of fabrication of resonant optical detection section of a sensor platform chip.
Figure 3C:
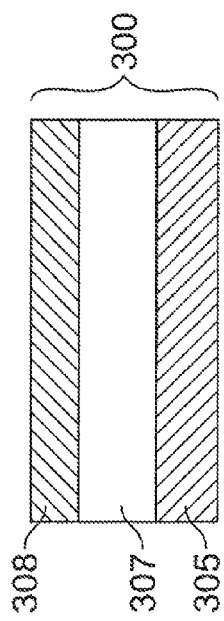
Figure 3B:
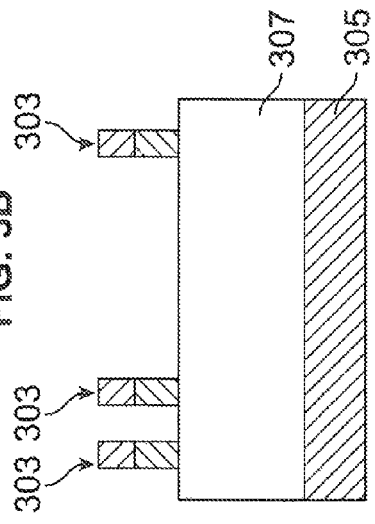
Figure 3D:
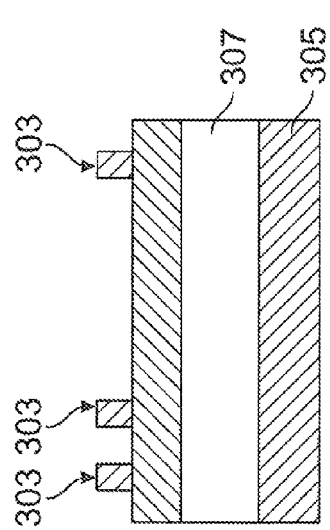
Figure 3E:
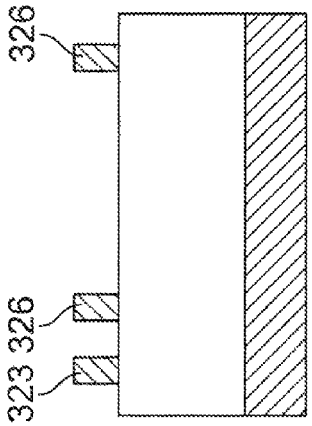

FIGS. 3a-e illustrates the optical resonator and optically coupled waveguide of FIG. 2c during various stages of manufacture. An SOI base 300 is provided in FIG. 3a, including a substrate layer 305 of silicon, an intermediate layer 307 of silica and a silicon layer 308. As shown in FIG. 3b, a thin layer of photoresist (PR) 302 can be deposited on silicon layer 308. The photoresist is photolithographically patterned into a waveguide-microring pattern 303 as shown in FIG. 3c. Finally the pattern is etched on the silicon using, for example, reactive ion etching (RIE) as shown in FIG. 3d, leaving the optical resonator 326 and waveguide 323 as shown in FIG. 3e.

EXAMPLE 2B

Sensor Platform Chip Fabrication

FIGS. 4a-4l illustrate stages of fabrication of the sensor platform. The sensor can be fabricated on a silicon-on-insulator (SOI) substrate to define the Si high-Q microring opical resonators optically decoupled from the nanofluidic FET separation/amplification section. That is, the high-Q Si optical microring resonators need to be placed on $SiO_2$ without any surrounding Si base that would otherwise connect the rings to the remaining Si on the chip. This entails, for example, two main masking steps in the fabrication to define the separation/amplification section first and then the resonant optical detection section.

Figure 4A:
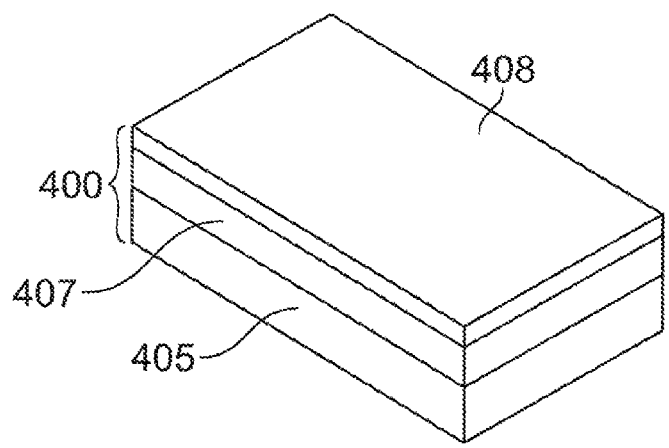
Figure 4B:
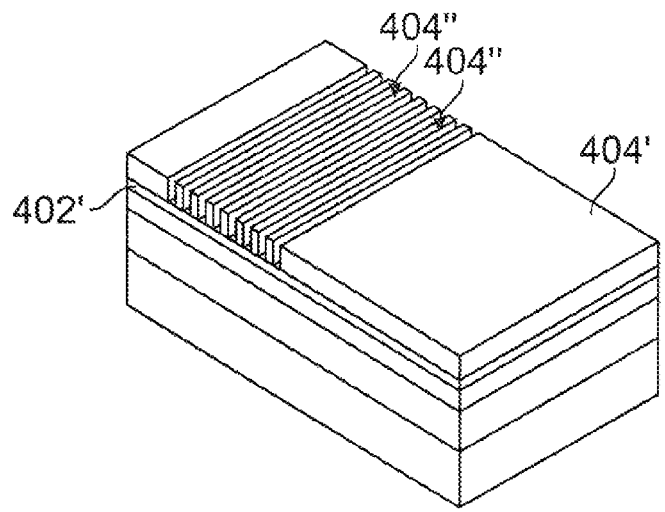

As shown in FIG. 4a, a clean, bare SOI substrate 400 is provided. The SOI substrate can include: a substrate layer 405, for example formed of a 200-500 nm thick Si layer; an intermediate layer 407, for example, formed of a 1-3 μm thick $SiO_2$ layer; and a top layer 408, for example, formed of a 300-500 μm commercial wafer of Si. As shown in FIG. 4b, a thin gate patterning layer 402' formed of $SiO_2$, for example, can be thermally grown on layer 408, and a gate-patterned photoresist layer 404' can be deposited on the thermally grown gate patterning layer 402. The gate-patterned photoresist layer 404' can be exposed and developed, and the exposed portions of gate patterning layer 402' underlying gate-patterned portions 404" of photoresist layer 404', can be etched away by reactive ion etching (RIE) to form gate patterns that extend through the gate-patterned photoresist layer 404', gate patterning layer 402 and abut a surface of top layer 408. Gate patterned photoresist layer 404' can be removed to expose gate patterning layer 402, with its gate patterns formed therein, to act as a mask for layer 408 during a dopant addition step described with respect to FIG. 4c.

Figure 4C:
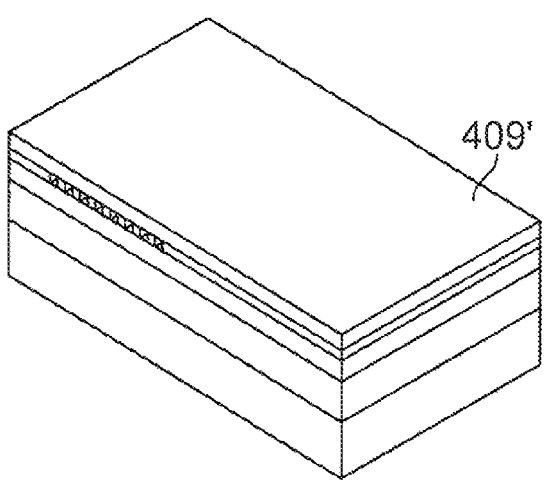
Figure 4D:
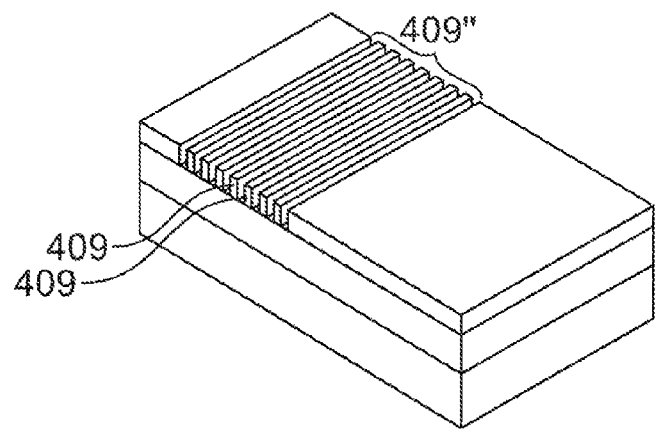

For example, as shown in FIG. 4c, a dopant layer 409' formed of, for example, borosilicate spin-on-glass (SOG), is deposited over gate patterning layer 402 and in the gate patterns thereof over the top layer 408. Boron dopant from the borosilicate spin-on-glass diffuses into portions of layer 408 underlying the gate patterns of gate patterning layer 402 to define gate region 409" that includes at least one gate 409. Dopant layer 409' as well as the gate patterning layer 402 can be removed, for example by exposure to HF as shown in FIG. 4d.

Figure 4E:
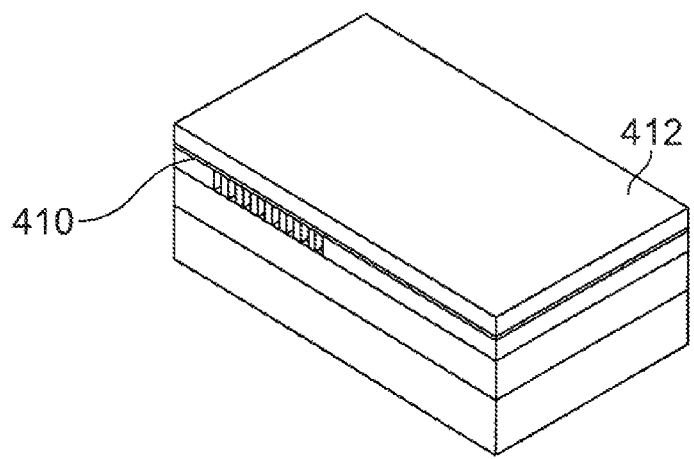
Figure 4F:
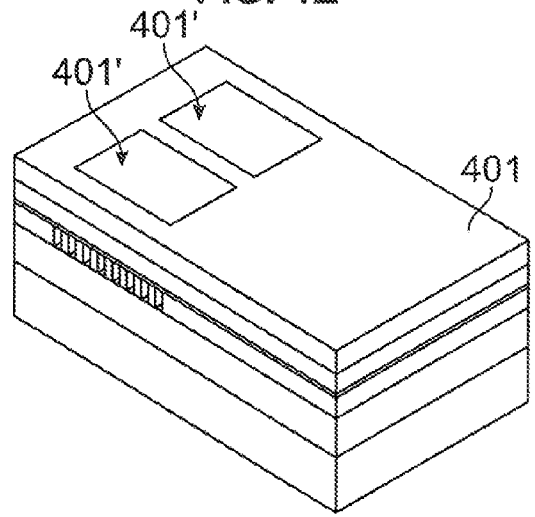

In FIG. 4e, an antireflective coating (ARC) layer 410' and a layer of PR 412 are formed, such as via spin-coating, over substrate 400, including over gate region 409" to form PR/ARC stack. As shown in FIG. 4f, portions of the PR/ARC stack under open areas 401' of a patterned contact mask 401 are exposed to a UV laser, to create a nanochannel pattern including a plurality of nanochannels (nanochannels not visible at this scale) using interferometric lithography (IL).

Figure 4G:
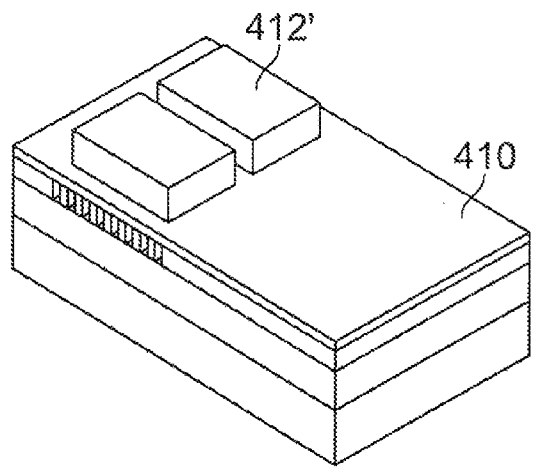

In FIG. 4g, developed PR nanochannel pattern 412' (nanochannels not visible at this scale) is shown with other portions of PR layer 412 removed to expose portions of ARC layer 410 including ARC at the channel bottom (not visible).

Figure 4H:
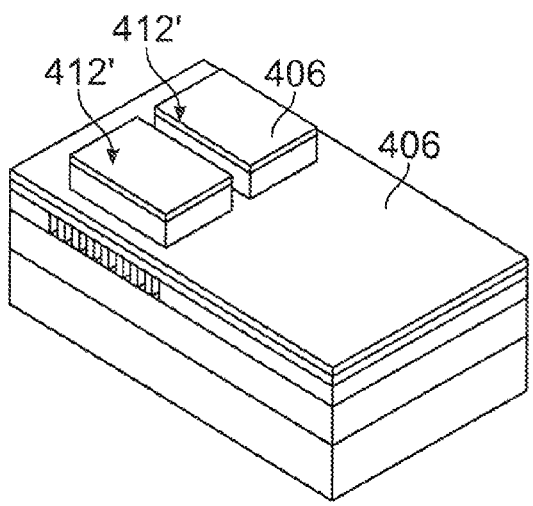

A lift-off layer 406, for example a metal layer such as a layer of chrome (Cr) can be sputter-deposited onto the remaining developed PR nanochannel pattern 412' as shown in FIG. 4h to form CR/PR stacks 412". The Cr/PR stacks can then be removed by lift-off in acetone (not shown), leaving a Cr/ARC nanochannel pattern including a plurality of CR/ARC nanochannels pattern strips. For example, the CR/ARC nanochannel pattern can serve as a hard mask that yields a negative image of the previously developed PR nanochannels pattern.

Figure 4I:
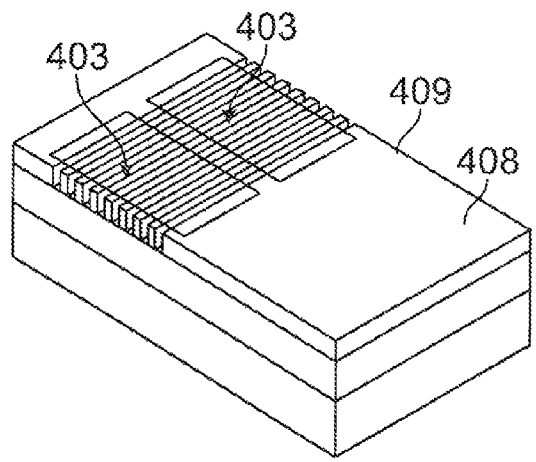

A $CHF_3$—$O_2$ plasma can then be then used to etch a plurality of high-aspect-ratio nanochannels 403', configured in a nanochannel pattern 403, into portions of the top Si layer 408 of the SOI substrate 400 that are not protected by the remaining CR/ARC layers. The magnitude of etching into the Si layer 408 is preselected such to prevent complete etching through the layer 408. In other words, etching is performed to form the nanochannels but to a depth that still preserves electrical continuity for the at least one gate 409 previously formed as shown in FIG. 4d. Gates 409 can extend substantially from one end of layer 408 to another end of layer 408 and are formed substantially perpendicular to a plurality of nanochannels formed in layer 408. An $O_2$ plasma is subsequently used to remove the remaining Cr and ARC as shown in FIG. 4i.

Figure 4J:
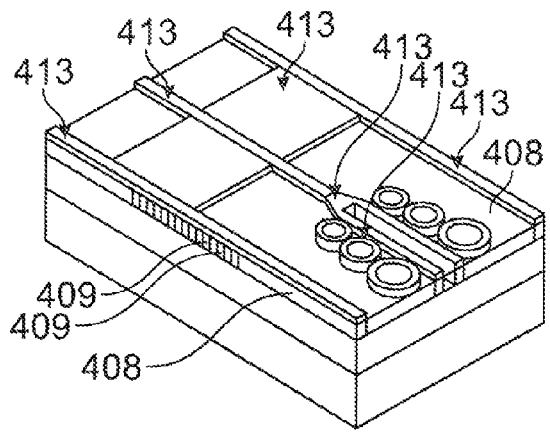
Figure 4K:
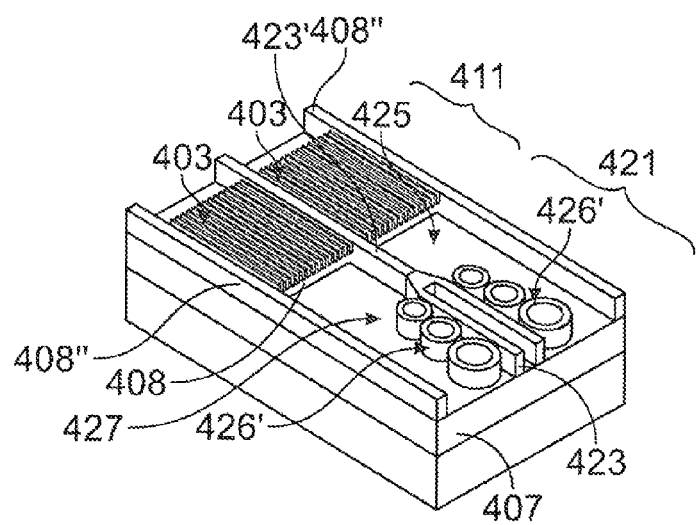

A photoresist layer, such as layer 302 as described above and shown in FIG. 3b, can be deposited over layer 408, and then patterned as described above and shown in FIG. 3a, into the waveguide-microring pattern 413 illustrated in FIG. 4j. The exposed portions 421 of Si layer 408 (i.e., those portions of 408 not covered by the waveguide-microring pattern 413) is removed by etching to expose the underlying portions 425, 427 of the $SiO_2$ layer 407, thereby defining the optical microring resonators 426' and 426", waveguide 423 including waveguide portions 423' and 423", and chamber sidewalls 408" as shown in FIG. 4k.

A top surface of all exposed features formed of Si can then be thermally oxidized (not shown). In other words, a top surface of the microrings, waveguides, nanochannels sidewalls and the chamber sidewalls can be thermally oxidized. For example, because the microrings, waveguides, nanochannels sidewalls and chamber sidewalls can be formed of a pattered layer, such as from a top silicon layer of an SOI substrate, these features can be formed of Si. A thermal oxidation of their surfaces will result in the formation of a layer of SiO2 at an upper portion of these features. Although not shown in FIGS. 4a-4l, and example of an oxidized layer formed on surfaces of the microrings, waveguides, nanochannels array and chamber sidewalls is shown in FIGS. 1c-e. In another example, rather than thermally oxidizing the top surfaces of these features, an insulating layer can be deposited over their top surfaces.

Figure 4L:
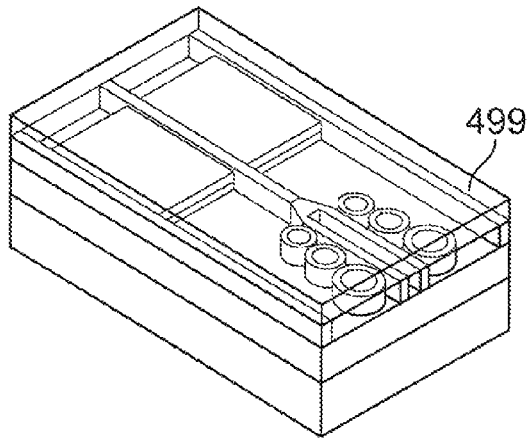

The entire substrate except for the rings is masked with PR for antibody immobilization as described in Example 2c below. Upon attaching the antibodies to the micro-rings as described in detail below in Example 2c, the PR is removed in acetone, and a cover layer 499 configured to protect the chip can be formed over a surface of the chip. For example, cover 499 can be formed of $SiO_2$ or pyrex. After thermally oxidizing the surface of the microrings, waveguides, nanochannels array and chamber sidewalls, the cover 499 can be anodically bonded to the oxidized Si layer (not shown) to seal over a top portion of the channels and the active and reference chambers as shown in FIG. 4l.

EXAMPLE 2C

Attaching Antibodies to Rings

Different antibodies can be attached to each of the at least one Si microrings. For example, cTnI, Myo, and CK-MB can be attached to a first Si microring, a second Si microring, and a third Si microring, respectively. This can be done by using UV to activate one of the ring's silicon surface while masking the other rings' surfaces. The first ring's surface is then soaked in pristine silicon in dilute (1%) HF solution to remove an oxidized layer thereof, while hydrogenating the Si surface, to produce unreactive silicon hydride ($SiH_x$; x=1, 2, or 3) termination that is unreactive to antibody immobilization. The HF exposure step can be incorporated into the fabrication method described above and shown in FIGS. 4a-4l, and can be performed after the formation of the waveguide and microrings shown in FIG. 4k and before addition of the cover 499 as in FIG. 4l. As described above the nanochannel region 411 can be masked to prevent any loss of the thermally grown $SiO_2$ and the duration of dilute HF exposure can be limited such that the underlying $SiO_2$ layer 407 in the SOI substrate 400 is only minimally etched. Next, the H-passivation can be locally removed using UV light at 254 nm by treating the surface with a solution of amine N-1-BOC-amino-3-cyclopentene (BACP) prepared in methanol (50 mg/mL, 50 µL/cm$^2$). This can induce the desired alkene attachment reaction on exposure to UV for 1.5 hrs. This results in BACP-terminated surfaces which are first treated with 25% trifluoroacetic acid (TFA) in $CH_2Cl_2$ for 2 hrs, then with 10% $NH_4OH$ for 7 min and finally with a bifunctional crosslinker, sulfo-succinimidyl 4-(N-maleimidomethyl) cyclohexane-1-carboxylate (SSMCC) which reacts with the amine groups that are formed after the $NH_4OH$ reaction. This can be carried out by covering the surface with 50 µL of a solution of SSMCC (1.5 mM in 150 mM triethanolamine buffer, pH 7) for 20 min. The SSMCC can then be allowed to react with the thiol groups that are present on the antibodies.

Monoclonal antibodies can then be immobilized on the exposed Si ring surfaces using the following procedure: 24 mL of toluene is flushed across the surfaces and allowed to react for 1 hr at room temperature. Then, 4% (v/v) glycidyloxypropyl trimethoxysilane (GPTMS) can be introduced in toluene and allowed to react for another hour. This reaction covalently attaches epoxy to the Si ring surfaces, which are then rinsed with acetone followed by 1×PBS buffer. A concentration of 1 mg/mL of the IgG can be applied on the Si ring surface and allowed to react overnight at room temperature. Finally, non-specifically bound IgG can be removed by washing the surfaces with 1×PBS buffer. The bound antibody can be characterized by contacting it with fluorescently labeled biomarkers to determine the surface density of active sites.

EXAMPLE 3

Operation and Use of a Sensor Platform System

Figure 5:
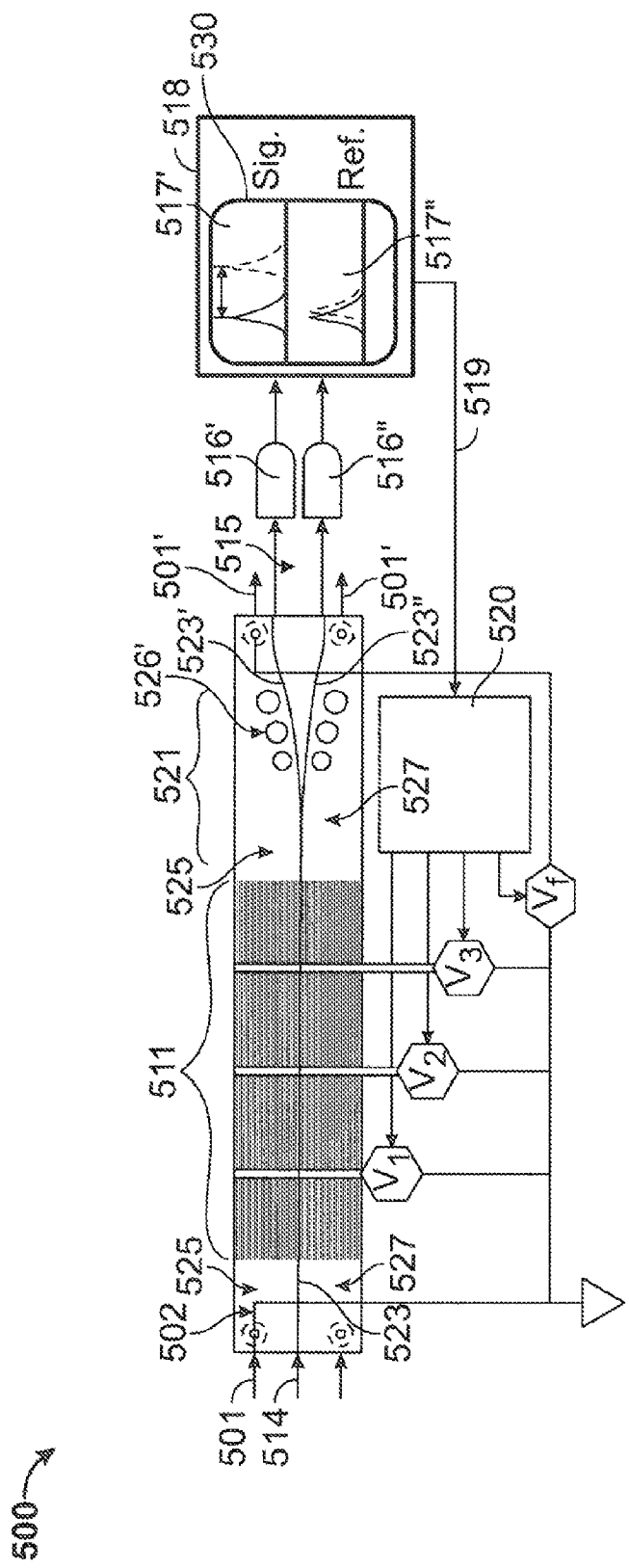
FIG. 5 shows a top view of an a sensor platform system, such as that shown in FIG. 1b, and illustrating a graphical representation, such as on a display, of a sample output signal as compared to a graphical representation of a reference output signal.

As illustrated in a top view shown in FIG. 5, a sensor platform 500 consists of two main sections that are integrated on a single SOI substrate (not visible). The main sections include a pre-processing FET nanochannel-array section 511 that enables controlled lateral flow of an analyte and separation/concentration of proteins provided from a sample, and a detection section 521 that includes optical resonators 126', such as high-Q optical Si microring resonators functionalized with antibodies that translate molecule-binding events to detectable changes in the transmitted optical signal.

For example, sample analyte is loaded (as indicated by arrows 501) into a ~10 µL reservoir 502 which is configured to provide the sample to remaining portions 525, 527 of the integrated sensor platform. From the reservoir 502, the analyte first passes through the pre-concentration/separation stage 511 where the concentration of target molecules is amplified, and the biomarkers are spatially separated along the channel using dynamic field-gradient focusing (DFGF). As a result, each focused band of proteins being eluted exits the separation stage (as indicated by arrows 501') at a predetermined time as controlled by the flow and separation control units 520.

The focused band of proteins flow around each, for example a first, second and third optical resonators, of the at least one optical microring resonators of a series microresonators 526' and 526". The microrings can be configured to have different diameters. To ensure that the detected resonant wavelength shift is due solely to protein binding and not temperature variations or impurities in the buffer solution, the sample flow can be divided between two microchambers (which can be parallel microchannels): an active analysis chamber 525 with functionalized optical resonators 526' (functionalized, for example, with antibody coating), and a reference chamber 527 with neutral optical resonators 526" (not functionalized with an antibody coating), and optical properties of the optical resonators of each respective chamber can be measured and compared. Accordingly, optical resonators 526' and 526", which can be ring shaped optical micro-ring resonators, in both the analysis and reference chambers, respectively, can be optically identical so that each of a pair of corresponding rings (i.e., a first ring of at least one ring 526' and a first ring of at least one ring 526"; a second ring of at least one ring 526' and a second ring of at least one ring 526"; and a third ring of at least one ring 526' and a third ring of at least one ring 526") have the same resonant wavelength in the absence of biomarker binding. Because the surface of each ring of the at least one ring 526' in the active analysis chamber can be coated with a respective at least one type of antibody associated with at least one associated biomarker (e.g., a cardiac biomarker), protein binding can be identified from the magnitude of a resonant optical wavelength shift that is measured as a function of a temporal variation of transmitted optical power as a wavelength of an input laser 514 is varied across a range of wavelengths, including a resonant wavelength of each of the at least one ring of rings 526' and rings 526".

For example, as described above, each ring can have a different diameter. Therefore, each ring has a corresponding one of different resonant wavelengths. Accordingly, optical properties of each ring can be monitored independently by scanning the input laser wavelength through a wide range of wavelengths, including resonant wavelengths of each resonator. Additionally, the input the optical power can be equally divided between two waveguides 523', 523", for example in the detection section 521 using a Y-branch waveguide. As a result, the optical output 515 power exiting a branch of the waveguide 523 optically coupled to respective optical resonators of a respective chamber can be monitored separately, for example as optical output 515' and 515". This can be done by using a respective one photodetectors 516' and 516" to generate signals 517' and 517" corresponding to the optical output of chambers 525 and 527. The optical outputs 515' and 515" can be compared, subtracting for noise or resonance shifts not caused by binding events, using an electronic processing circuit or processor 518. The outcome of this differential sensing scheme, for example via examination of an output on a display 530, such as an oscilloscope, can reveal the presence of target molecules bound to the surface of the corresponding at least one ring 526', and consequently, their concentration in the analyte, with a large signal-to-noise ratio.

Although the optical output power of each waveguide and the differential signal can be monitored using an oscilloscope as described above and/or be partially automated via manual controls that can be electronically coupled via 519 to an electrode potential source 520 which can control electrode potentials V1, V2 and V3, or an electric field Vf to control a flow rate of the sample.

Figure 6:
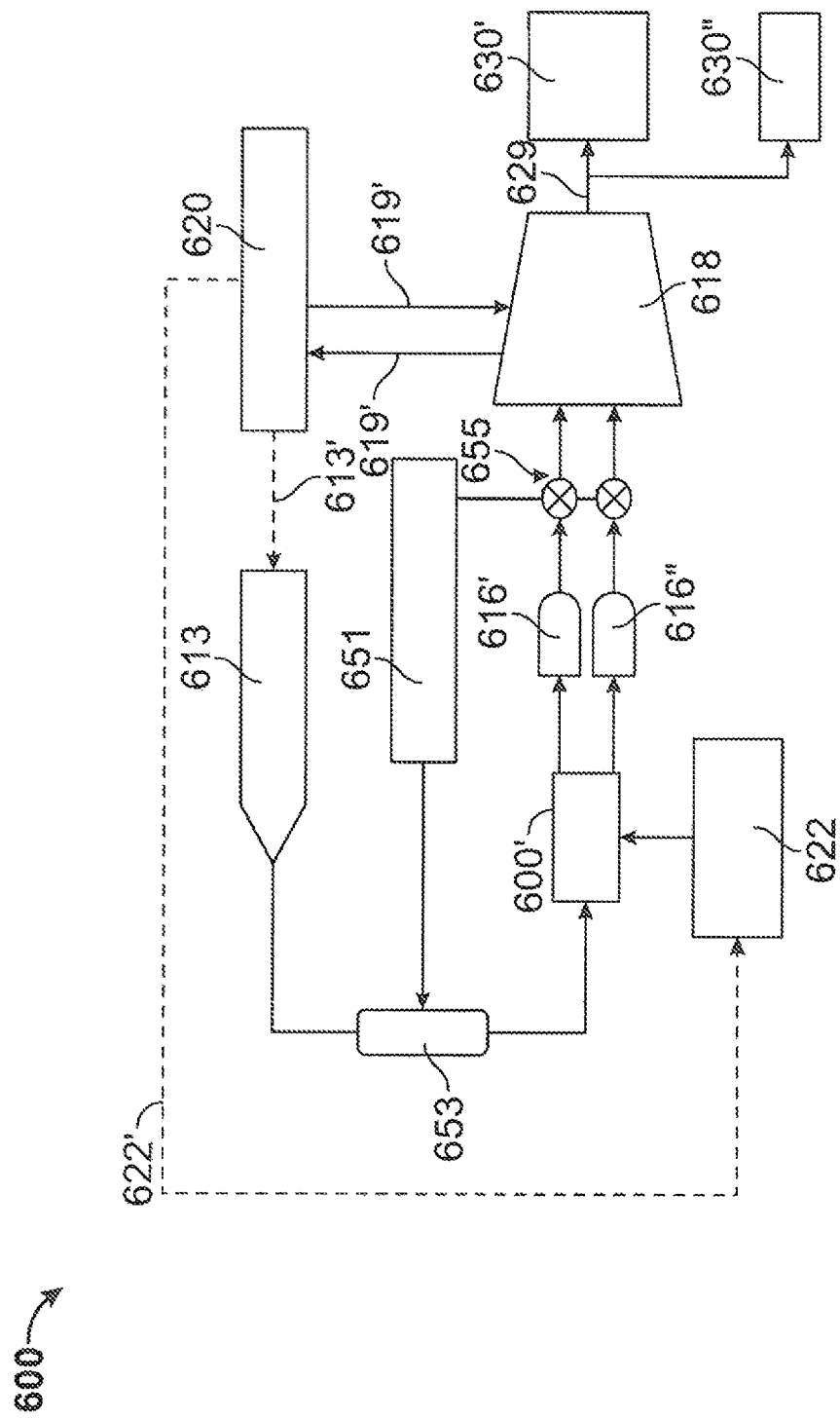
FIG. 6 provides an alternate representation of an automated sensor platform system.

A fully automated sensor platform can include an electronic system that can be used to translate the resonant shifts into an electronic differential signal. For example, FIG. 6 shows a diagram of the fully automated sensor platform 600 including a Pound-Drever-Hall (PDH) system, consisting of an electronic oscillator 651, optical phase modulator 653 and two RF mixers 655, that is used to generate a signal proportional to the resonant wavelength shift in SOI chip 600' as detected by detectors 616', 616". The signal-processing unit 618 can generate the differential signal (using, for example, an operational amplifier) and conditions an output signal 629 to be displayed on a display 630', such as an LCD display, and/or to be transmitted to an input 630", such as a USB port, of a computer. A main control unit 620 connected 613', 622', 619' to the laser 613, flow and separation control unit such as a voltage source 622, and processing unit 618, respectively, can manage the operation of the entire system to maintain maximum sensitivity.

All electronic systems and the optical phase modulator shown in FIG. 6 can be monolithically fabricated on the same SOI chip along with the nanochannels and micro-rings using CMOS technology. The laser and photodetectors can be the only external elements that can be mounted on the main silicon substrate using well-known hybrid integration techniques currently used in silicon photonics.

EXAMPLE 4

Sensitivity and Dynamic Range

The lower detection limit of optical microring resonators depends on the number of active binding sites on the microring surface ($N_a$), binding probability for a given analyte flow velocity ($P_v$), optical quality factor of the microring ($Q_L$), excess optical polarizability ($\alpha_{ext}$) of target molecules, laser input power, and the photodetector sensitivity. $N_a$ and $P_v$ can be estimated based on the microring and detection chamber dimensions, but $\alpha_{ext}$ for cardiac biomarkers is not known. While not limited to a particular method of experimentation or theory, the detection limit of an Si optical microring resonator with diameter of 50-100 μm, a thickness of 0.4 μm and $Q_L$ of $10^5$ can be estimated to be about 0.04 fg, or about 1000 troponin molecules.

The number of molecules that saturate the binding sites of antibody-coated optical resonators can be set equal to $N_a$. While not limited to a particular method, based at least on the antibody molecules size, an evaluation of surface coverage and activity of antibodies, a value of $N_a$ for a 70 μm diameter silicon microring can be estimated as about one million sites. This means 40 fg of troponin is needed to occupy all the binding sites on the ring. With an amplification factor of 1000 for the focusing stage of a sensor platform, and assuming that, at a flow rate of 5 mm/min, about 50% of the molecules passing through the detection chamber bind to the active sites, the sensitivity and dynamic range of the system can be quantified.

Figure 7:
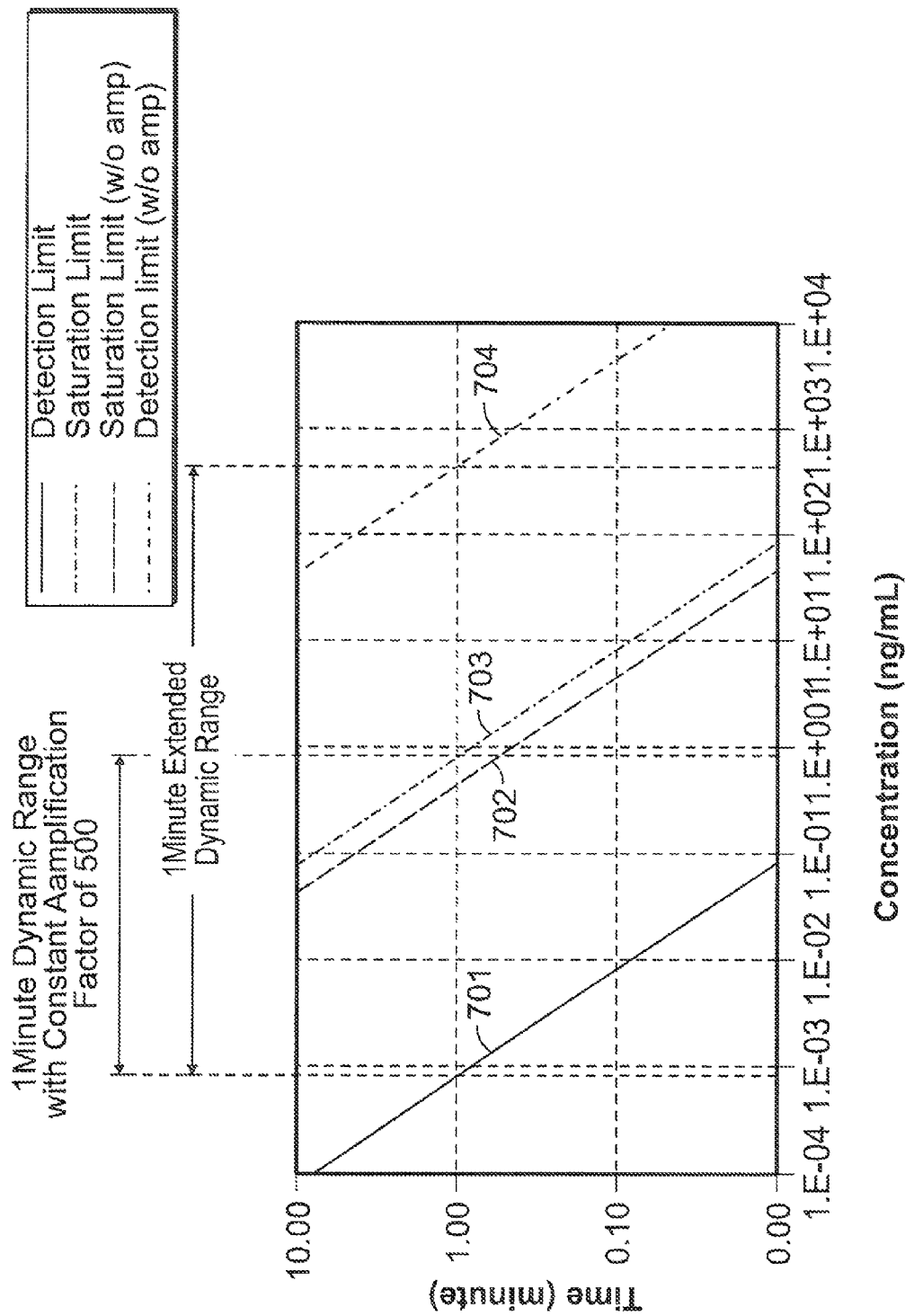
FIG. 7 provides a graph of a required measurement time plotted against a molecule concentration for minimum detection limit as well as the saturation limit.

For example, FIG. 7 shows the required measurement time, i.e., exposure time of a microring to a concentrated solution, plotted against the molecule concentration for minimum detection limit (line 701) as well as the saturation limit (line 703). Concentrations as low as 1 pg/mL can be detected in less than 1 minute. The estimated dynamic range, with constant pre-concentration amplification, is equal to the dynamic range of the microring, approximately 3 orders of magnitude. However, by switching off the amplification for high concentration limits, the dynamic range can be extended by 2 orders of magnitude resulting in a total dynamic range of 5 orders of magnitude.

In FIG. 7, the dashed lines 702 and 704 indicate the sensitivity/saturation limits and detection limits, respectively, for the rings alone without nanofluidic amplification. The extended dynamic range starts from line 701 and ends at the dashed 704. Faster measurements can extend the upper limit and longer measurement times can extend the lower limit. The measurement time can be controlled with high accuracy due to the presence of FET nanochannels that enable control over the time when each peak is delivered to the rings.

The maximum volume of the sample that flows through the device, including both the active and passive channels, for detection of 1 pg/mL is 0.2 nL. These estimates are for values of $Q_L \sim 10^5$, and concentration by a factor of 1000.

While the invention has been illustrated respect to one or more implementations, alterations and/or modifications can be made to the illustrated examples without departing from the spirit and scope of the appended claims. In addition, while a particular feature of the invention may have been disclosed with respect to only one of several implementations, such feature may be combined with one or more other features of the other implementations as may be desired and advantageous for any given or particular function.

For example, some embodiments of a sensor platform have been described as a combination of a nanofluidic amplification section and a resonant optical detection section. Although these sensor configurations are described and shown as having specific configurations for microfluidic separation/amplification and resonant optical detection/quantification (i.e. SOI nanochannels and SOI microrings, respectively), other embodiments can be implemented using other configurations.

For example, nanochannels can be formed based on polymers or semiconductor materials other than silicon. Additionally, nanochannels arrays can include various configurations and numbers of electrodes, or can even be formed without electrodes.

The optical resonators and waveguides are not limited to silicon. In other examples, the microring resonators, waveguides and/or chamber sidewalls can be formed of poly (methyl methacrylate) (PMMA). Integrated optical microresonators can be based on silicon nitride, III-V semiconductors and polymers. Other types of optical microresonators, including microdisks and photonic crystals (one or two dimensional) can also be used. Off-chip and on-chip optical microresonators can be used, including microsphere, microcapillary, microtorooid, and fiber based (such as fiber-Bragg gratings).

The embodiments described herein are capable of fast, accurate and sensitive detection of cardiac biomarkers on a chip for the diagnosis of cardiac diseases. Additionally, sensor configuration of the embodiments can be used for detecting a variety of biomarkers (other than cardiac biomarkers). For example, an embodiment can include changing the type of antibody used for functionalizing the microrings in the active channel. Furthermore, more than one of micro-rings can be used in the analysis chamber for simultaneous analysis of many biomarkers in a compact system.

The platform system can also include a mechanism different than a Pound-Drever-Hall mechanism. For example, a broadband source of electromagnetic energy can be used instead of a tunable laser.

Embodiments described herein can be configured for use in optofluidic-integrated systems that have application beyond sensing. For example, the nanochannels can be used for accepting DNA and the high-Q optical micro-rings may result in functionalities capable of being utilized, as described above, for the analysis thereof.

In an example, a system is provided to which a sample is provided. To increase the density of target proteins, the system performs a separation/amplification in nanochannels based on differences of electrophoretic mobilities for different proteins. To detect the target proteins with high sensitivity (via high-Q optical resonance) and specificity (via immunoafinity), there is provided resonant optical detection based on resonant wavelength shift due to interaction of target molecules with the evanescent optical field of a functionalized high-Q optical microresonator. The system includes a readout mechanism for measuring wavelength shift. The system also provides results, including a concentration of target molecules in the sample.

It is noted that, as used in this specification and the appended claims, the singular forms "a," "an," and "the," include plural referents unless expressly and unequivocally limited to one referent. Thus, for example, reference to "a platform" includes two or more different platforms. Furthermore, to the extent that the terms "including", "includes", "having", "has", "with", or variants thereof are used in either the detailed description and the claims, such terms are intended to be inclusive in a manner similar to the term "comprising." As used herein, the phrase "one or more of", for example, A, B, and C means any of the following: either A, B, or C alone; or combinations of two, such as A and B, B and C, and A and C; or combinations of three A, B and C.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A sensor platform comprising:
   a substrate;
   a plurality of nanochannels disposed on the substrate;
   a plurality of electrodes, each electrode extending across a width of the plurality of nanochannels;
   a waveguide disposed on the substrate;
   an analysis chamber and a reference chamber disposed on the substrate;
   at least one analysis optical resonator disposed in the analysis chamber and optically coupled to at least a portion of the waveguide, the at least one analysis optical resonator in fluid communication with at least one of the plurality of nanochannels; and
   at least one reference optical resonator disposed in the reference chamber and optically coupled to at least a portion of the waveguide, the at least one reference optical resonator in fluid communication with at least one other of the plurality of nanochannels,
   wherein the waveguide comprises:
      a first portion that separates the at least one of the plurality of nanochannels that is in fluid communication with the at least one analysis optical resonator from the at least one other of the plurality of nanochannels that is in fluid communication with the at least one reference optical resonator; and
      a second portion comprising a first leg in optical communication with the at least one analysis optical resonator and a second leg in optical communication with the at least one reference optical resonator.

2. The sensor platform chip of claim 1, wherein at least a portion of the plurality of electrodes is in contact with a portion of the plurality of nanochannels.

3. The sensor platform chip of claim 1, wherein at least one of the plurality of electrodes is doped at selected areas of the substrate.

4. The sensor platform chip of claim 1, wherein at least one of the plurality of electrodes comprises a boron doped portion of a silicon layer of the substrate.

5. The sensor platform chip of claim 1, wherein the at least one analysis optical resonator comprises a plurality of optical microring resonators, each of the optical microring resonators having a different diameter than other of the optical microring resonators in the analysis chamber.

6. The sensor platform chip of claim 1, wherein the at least one reference optical resonator comprises a plurality of optical microring resonators, each of the optical microring resonators having a different diameter than other of the optical microring resonators in the reference chamber.

7. The sensor platform chip of claim 1, wherein an outer surface of the at least one analysis optical resonator is coated with at least one antibody.

8. The sensor platform chip of claim 1, wherein an outer surface of the at least one analysis optical resonator is coated with cardiac troponin-I (cTnl), myoglobin (Myo), or creatine kinase MB (CK-MB).

9. The sensor platform chip of claim 1, wherein the substrate comprises an SOI substrate.

10. A lab-on-a-chip system, comprising:
    a substrate;
    a plurality of nanochannels disposed on the substrate;
    a plurality of electrodes, each electrode extending across a width of the plurality of nanochannels;
    a waveguide disposed on the substrate;
    an analysis chamber and a reference chamber disposed on the substrate; at least one analysis optical resonator disposed in the analysis chamber and optically coupled to at least a portion of the waveguide, the at least one analysis optical resonator in fluid communication with at least one of the plurality of nanochannels; and
    at least one reference optical resonator disposed in the reference chamber and optically coupled to at least a portion of the waveguide, the at least one reference optical resonator in fluid communication with at least one other of the plurality of nanochannels;
    an optical input source for providing an electromagnetic energy input to the waveguide;
    at least one photodetector for receiving an electromagnetic energy output from the waveguide;
    an electrode potential source that controls electrode potentials;
    a processor in electronic communication with the at least one photodetector and a controller in electronic communication with the processor, the optical input source, an electrode potential source, the electrode potential source in electronic in communication with at least one of the plurality of electrodes,
    wherein the waveguide comprises:
       a first portion that separates the at least one of the plurality of nanochannels that is in fluid communication with the at least one analysis optical resonator from the at least one other of the plurality of nanochannels that is in fluid communication with the at least one reference optical resonator; and a second portion comprising a first leg in optical communication with the at least one analysis optical resonator and a second leg in optical communication with the at least one reference optical resonator.

11. The system of claim 10, further comprising a display for displaying an output generated by the processor.

12. The system of claim 10, wherein the controller, the optical input source and electrode potential source comprise a feedback loop for adjusting electrode potentials of the plurality of electrodes and for adjusting an optical input wavelength of the electromagnetic energy provided by the optical input source to the waveguide.

13. The system of claim 10, wherein the plurality of electrodes comprises a first electrode, a second gate and a third electrode.

\* \* \* \* \*